US011923090B2

(12) United States Patent
Shin et al.

(10) Patent No.: US 11,923,090 B2
(45) Date of Patent: Mar. 5, 2024

(54) EARLY SKIN CONDITION DIAGNOSTICS USING SONIC SENSORS

(71) Applicant: Google LLC, Mountain View, CA (US)

(72) Inventors: Dongeek Shin, Mountain View, CA (US); William James Biederman, Mountain View, CA (US); Shwetak Patel, Seattle, WA (US)

(73) Assignee: GOOGLE LLC, Mountain View, CA (US)

( * ) Notice: Subject to any disclaimer, the term of this patent is extended or adjusted under 35 U.S.C. 154(b) by 290 days.

(21) Appl. No.: 17/379,356

(22) Filed: Jul. 19, 2021

(65) Prior Publication Data
US 2022/0020494 A1 Jan. 20, 2022

Related U.S. Application Data

(60) Provisional application No. 63/053,343, filed on Jul. 17, 2020.

(51) Int. Cl.
*G06Q 30/00* (2023.01)
*G06N 20/00* (2019.01)
*G16H 50/20* (2018.01)

(52) U.S. Cl.
CPC ............. *G16H 50/20* (2018.01); *G06N 20/00* (2019.01)

(58) Field of Classification Search
None
See application file for complete search history.

(56) References Cited

U.S. PATENT DOCUMENTS

| 10,438,040 | B2 | 10/2019 | Strohmann et al. | |
|---|---|---|---|---|
| 2017/0151425 | A1* | 6/2017 | Redding, Jr. | A61M 37/0092 |
| 2019/0037642 | A1* | 1/2019 | Price | H04N 21/25866 |
| 2019/0307335 | A1* | 10/2019 | Bruce | A61B 5/02055 |
| 2021/0256100 | A1* | 8/2021 | Grover | G06V 40/1376 |

OTHER PUBLICATIONS

Auksorius et al., "Fast subsurface fingerprint imaging with full-field optical coherence tomography system equipped with a silicon camera", Journal of Biomedical Optics, Sep. 8, 2017, vol. 22, No. 9, 9 pages.

(Continued)

*Primary Examiner* — Matthew T Sittner
(74) *Attorney, Agent, or Firm* — Dority & Manning, P.A.

(57) ABSTRACT

Computing systems and methods are provided for detecting skin conditions of humans. A computing device can authenticate a user via a fingerprint scan of a first skin region of the user using a three-dimensional (3D) sonic sensor. The device can generate a three-dimensional (3D) volumetric sonic measurement of a second skin region of the user based at least in part on one or more sonic pulses of the three-dimensional sonic sensor. The device can input data indicative of the 3D volumetric sonic measurement into one or more machine-learning models, generate one or more skin cancer condition identifications associated with the second skin region of the user based on one or more outputs of the one or more machine-learned models, and provide one or more outputs including the one or more skin cancer condition identifications associated with the second skin region of the user.

20 Claims, 15 Drawing Sheets

(56) References Cited

OTHER PUBLICATIONS

Bard, "High-Frequency Ultrasound Examination in the Diagnosis of Skin Cancer", Dermatologic Clinics, Oct. 2017, vol. 35, No. 4, pp. 505-511.
Dascalu et al., "Skin cancer detection by deep learning and sound analysis algorithms: A prospective clinical study of an elementary dermoscope", EBioMedicine, May 14, 2019, vol. 43, 18 pages.
Dolcourt, "Galaxy S10 has an ultrasonic fingerprint scanner. Here's why you should care", Feb. 23, 2019, https://www.cnet.com/news/galaxy-s10-has-ultrasonic-fingerprint-scanner-heres-why-you-should-care-explainer/, retrieved on Apr. 13, 2021, 5 pages.
Fenster et al., "3D Ultrasound Imaging in Image-Guided Intervention", Advancements and Breakthroughs in Ultrasound Imaging, IntechOpen, Jun. 5, 2013, 25 pages.
Majumder et al., "Smartphone sensors for health monitoring and diagnosis", Sensors, May 9, 2019, vol. 19, No. 9, 53 pages.
Pitat et al., "Skin melanoma imaging using ultrasonography: a literature review", Advances in Dermatology and Allergology, Jun. 3, 2018, vol. XXXV, No. 3, pp. 238-242.
Qualcomm, "Qualcomm 3D Sonic Sensor: ultrasonic security solution", 2021, https://www.qualcomm.com/products/features/fingerprint-sensors, retrieved on Nov. 4, 2021, 5 pages.

\* cited by examiner

EARLY SKIN CONDITION DIAGNOSTICS USING SONIC SENSORS

RELATED APPLICATIONS

This application is based on and claims benefit of U.S. Provisional Patent Application No. 63/053,343, titled "Early Skin Condition Diagnostics Using Sonic Sensors," filed on Jul. 17, 2020, which is hereby incorporated by reference herein in its entirety.

FIELD

The present disclosure relates generally to computer-implemented systems using sensors for diagnostics of skin conditions such as cancer.

BACKGROUND

Melanoma, a type of skin cancer, is known to be one of the most unpredictable tumors, because of its high variability in morphology. In some cases, even experienced dermatologists can give conflicting diagnostics results based on visual analysis of skin lesion surface (reference). Thus, medical imaging tools such as optical coherence tomography (OCT) or ultrasonography, that perform in vivo imaging of below the dermis layer to clearly differentiate skin cancer from other non-malignant conditions is helpful. However, these tools may be expensive and not readily available to the average consumer for easy check-ups to take early preventive action for detecting melanoma and other skin conditions.

SUMMARY

Aspects and advantages of embodiments of the present disclosure will be set forth in part in the following description, or may be learned from the description, or may be learned through practice of the embodiments.

According to one example aspect of the present disclosure, a computer-implemented method for generating skin condition diagnostics includes authenticating, by one or more processors of a user computing device, a user via a fingerprint scan of a first skin region of the user using a three-dimensional (3D) sonic sensor of the user computing device. The method includes generating, by the one or more processors, a three-dimensional (3D) volumetric sonic measurement of a second skin region of the user based at least in part on one or more sonic pulses of the 3D sonic sensor. The method includes inputting, by the one or more processors, data indicative of the 3D volumetric sonic measurement into one or more machine-learning models configured to identify one or more skin conditions in response to one or more 3D volumetric sonic measurement inputs. The method includes generating, by the one or more processors based on one or more outputs of the one or more machine-learned models, one or more skin condition identifications associated with the second skin region of the user. The method includes providing, by the user computing device, one or more outputs including the one or more skin condition identifications associated with the second skin region of the user.

According to another example aspect of the present disclosure, a computing device includes one or more three-dimensional (3D) sonic sensors, one or more processors, and one or more non-transitory computer-readable media that collectively store instructions that when executed by the one or more processors cause the one or more processors to perform operations. The operations include generating a three-dimensional (3D) volumetric sonic measurement of a skin region of a user based at least in part on one or more sonic pulses of the one or more 3D sonic sensors, inputting data indicative of the 3D volumetric sonic measurement into one or more machine-learning models configured to identify one or more skin conditions in response to one or more 3D volumetric sonic measurement inputs, generating, based on one or more outputs of the one or more machine-learned models, one or more skin condition identifications associated with the skin region of the user, and providing one or more outputs including the one or more skin condition identifications associated with the skin region of the user.

According to yet another example aspect of the present disclosure, one or more non-transitory computer-readable media store computer instructions, that when executed by one or more processors, cause the one or more processors to perform operations. The operations include generating a three-dimensional (3D) volumetric sonic measurement of a skin region of a user based at least in part on one or more sonic pulses of one or more 3D sonic sensors, inputting data indicative of the 3D volumetric sonic measurement into one or more machine-learning models configured to identify one or more skin conditions in response to one or more 3D volumetric sonic measurement inputs, generating, based on one or more outputs of the one or more machine-learned models, one or more skin condition identifications associated with the skin region of the user, and providing one or more outputs including the one or more skin condition identifications associated with the skin region of the user.

Other example aspects of the present disclosure are directed to systems, apparatus, computer program products (such as tangible, non-transitory computer-readable media but also such as software which is downloadable over a communications network without necessarily being stored in non-transitory form), user interfaces, memory devices, and electronic devices for generating diagnostic indications of skin conditions using sonic sensors.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which:

FIG. 7 depicts a diagram illustrating a skin cancer that penetrates dermal layers over time while the surface characteristics can appear similar;

DETAILED DESCRIPTION

Figure 1:
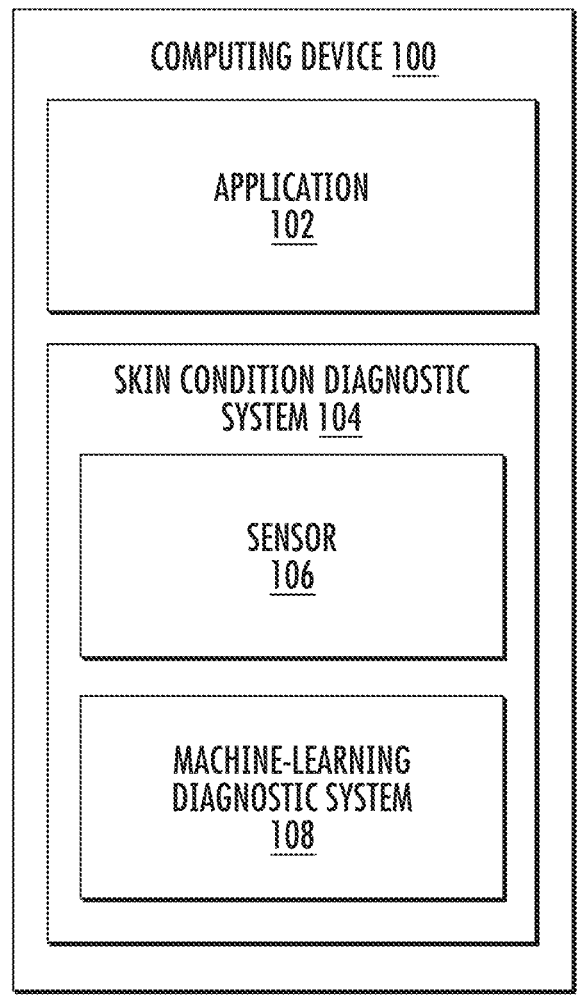
FIG. 1 depicts a block diagram of an example computing device in accordance with example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

The present disclosure is directed to a skin condition diagnostic system that leverages machine learning and sensors such as sonic fingerprint sensors to provide accurate skin condition identifications using consumer-level devices such as smartphones. In accordance with example embodiments, a sonic fingerprint sensor generates sonic data that is processed to generate volumetric data including depth information. The volumetric data is then analyzed using machine-learning techniques to generate accurate diagnostics of skin conditions such as skin cancer.

Traditional diagnostic tools such as optical coherence tomography (OCT) or ultrasonography tools are typically not readily available to the average consumer to perform check-ups to take early preventative action. Moreover, these tools often require a skilled technician to operate and observe data in order to make even a preliminary assessment of potential conditions such as cancers associated with a skin region of a user.

In accordance with example embodiments of the present disclosure, readily available sensors such as sonic fingerprint sensors included with many smartphones are utilized in combination with machine learning techniques to provide accurate diagnostics of skin conditions such as skin cancer. According to an example aspect of the present disclosure, a three-dimensional (3D) sonic fingerprint sensor can generate a 3D volumetric sonic measurement of a skin region of a user. In some examples, the 3D sonic fingerprint sensor can be a 3D ultrasonic fingerprint sensor and the 3D volumetric sonic measurement can be a 3D volumetric ultrasonic measurement. The 3D volumetric sonic measurement is generated using a combination of beamforming to generate high resolution measurement data in lateral and longitudinal directions and time resolution processing to generate depth information indicative of a skin condition volume below an outer skin surface. The 3D volumetric sonic data can be provided as input to one or more machine-learned models configured to identify one or more skin cancer conditions based on 3D volumetric sonic data.

In accordance with example embodiments, a 3D ultrasonic sensor of a computing device is used to generate three-dimensional volumetric data that is indicative of skin features both at the outer surface of the user's skin and below the skin surface. Back-reflection of sonic pulses at the outer surface of the skin can be measured to generate lateral data (e.g., x-direction) and longitudinal data (e.g., y-direction) indicative of skin features at the outer surface of the user's skin. A pulse entering the below-surface region of the user's skin results in sub-surface scattering. Back-reflection of the pulse entering the below-surface region can be measured to generate depth data indicative of skin features in the below-surface region of the user's skin. The received waveform(s) that result from the backscattering can be time resolved to determine depth data associated with the surface skin features. Moreover, the received waveform is the integral energy of pulses that are back-reflected at one or more epidermal and/or dermal layers below the outer surface. Thus, the received waveform is not simply a time-shifted version of the original waveform. Rather, its integral energy is indicative of the sub-surface skin properties. Typically, such back-scattered pulses are simply ignored by fingerprint sensors and the like that are focused on measuring outer surface features such as a fingerprint's ridges and valleys. By contrast, the present disclosure leverages the time-resolved properties of the received waveform(s) to provide a sonic measurement in three dimensions that is indicative of the properties both at and below the surface of a skin region of a user.

Three-dimensional volumetric sonic data generated in response to a scan of a skin region of a user can be processed using various machine-learning techniques to identify skin conditions such as skin cancers. According to an example aspect of the present disclosure, a sparse dictionary machine learning approach to identify skin cancer responses is provided. A dictionary of skin cancer or other features can be constructed in a three-dimensional sonic sensing domain and an optimization problem can be enforced using machine-learning to find a representation in the dictionary that best matches or fits to input volumetric sonic data. In example embodiments, the dictionary can be constructed using sensor data that is generated using a sonic sensor having a higher resolution than the sonic sensor of the computing device that is used to scan a user. By way of example, the sonic sensor of a computing device such as a smartphone for scanning a user may include an array of tens to thousands of transducers (e.g., 5×5-50×50 arrays) while a laboratory device used to generate the dictionary may include may more transducers such as thousands to millions of transducers (e.g., 100×100 array). In this manner, a more accurate representation of skin cancer features can be used by the model when comparing to input data.

In accordance with example embodiments, the machine-learning system may apply forward voxel blurring to the dictionary of skin features to simulate voxel blurring associated with the 3D sonic sensors of user computing devices. It may be observed that a voxel blurring phenomenon can occur in a consumer-level sonic sensor because of non-linear sub-surface ultrasonic scattering. For instance, a widened, dispersion-suffering pulse may be observed as a result of this non-linear scattering. Such blurring can lead to very little visual separation between a skin cancer such as melanoma and a non-skin cancer such as non-melanoma when compared to the true representation where the increased depth of the feature can be observed as a strong cue for diagnostics.

According to an example aspect of the present disclosure, a machine-learning system enforces an optimization problem to find a skin feature representation in the dictionary that most closely matches the feature(s) of the skin region of the user represented by the input volumetric data. As an example, an iterative shrinkage thresholding method can be used to solve an optimization with deterministic convergence. For instance, a gradient descent can be computed on a data loss term representing the difference between the dictionary feature and the user skin feature. A proximal map can then be computed and these two operations iterated until a convergence rule is met. By enforcing an optimization in this manner, a recovery of the true cell volumes from the dispersion-corrupted volumetric sonic measurements can be provided.

A sparse dictionary learning approach enables a consumer-level computing device to generate diagnostics whose logic and process can be observable by a clinician. By way of example, the machine-learning diagnostic system can provide an output indicative of one or more skin cancer features from the dictionary that were the basis for the diagnosis. In this manner, a clinician such as a doctor or other professional may assess the process by which the system generated diagnostic data. As such, the clinician not only has access to the final output but also the process and data underlying the diagnostic. Such an approach can enable a clinical and technical evaluation of the output that may be useful in a final determination by the clinician making an assessment.

According to some example aspects, an end-to-end machine-learned model is provided that takes as input raw volumetric ultrasonic data and generates as an output one or more indications of skin condition(s). A machine-learned detection or classification approach can be provided to identify skin conditions directly in response to 3D volumetric ultrasonic data. In this example, a dictionary of skin condition features is not necessarily provided. The end-to-end model may operate without an on-device dictionary of skin cancer features. Rather, the model may be trained using high and/or low resolution ultrasonic data to make inferences such as classifications of the input data. The training data can be annotated to indicate skin conditions. A supervised or semi-supervised learning approach can be used to train the model to identify skin cancer conditions.

Embodiments in accordance with the present disclosure provide a number of technical effects and benefits. By way of example, beamforming to generate sensor data using small transducer arrays, time-resolution of sensor data, and/or machine-learning techniques can be used independently or together to leverage relatively small and cost-effective sonic sensors for accurate in-field diagnostics of skin conditions such as cancers. Traditional sensor-based systems for skin condition diagnostics utilize large transducer arrays that operate in relatively low frequency ranges (e.g., 1-6 MHz). These devices may operate in continuous doppler modes to generate high resolution images. Thus, these devices are not small consumer operable devices. By the nature of the components involved, the devices tend to be large and expensive. Moreover, a skilled technician is often required for operation and a skilled clinician required to observe the data for making accurate diagnostics.

According to example embodiments of the present disclosure, relatively small and inexpensive transducers can be leveraged to provide automatic diagnostic information. By way of example, beamforming and time-resolution of back-scattered pulses can be employed to increase the resolution of the transducer array. The transmitted beam can be steered spatially using time delay or other techniques. Beamsteering can be accomplished in both lateral (x) and longitudinal (y) directions. Moreover, sub-surface scattering of pulses entering a sub-surface region can be measured by time-resolving back-reflection of the pulse(s). In this manner, a higher resolution volumetric measurement can be provided to generate ultrasonic data in three dimensions. By generating depth information, the system can resolve volume density to provide higher clinical accuracy than simple surface imagers such as cameras that take images of the skin. In some examples, the transducer array can operate at frequencies higher than conventional sonography systems. For example, the transducer array may operate at a frequency of about 50 MHz in some embodiments. In yet other examples, other frequencies higher than 6 MHz can be used.

Further, machine-learning techniques are provided to accurately determine skin conditions from the volumetric ultrasonic data. According to example embodiments, a sparse dictionary learning approach is provided that enables on-device learning of a closest match between input sensor data and high resolution data in a dictionary of skin cancer features. High resolution data can be used to generate the dictionary, and the machine-learning system can enforce an optimization problem to find a representation that provides the closest match to the input data. Such an approach can overcome the voxel blurring phenomenon sometimes associated with lower resolution transducer arrays.

In some implementations, in order to obtain the benefits of the techniques described herein, the user may be required to allow the collection and analysis of sensor data associated with the user or their device. For example, in some implementations, users may be provided with an opportunity to control whether programs or features collect such information. If the user does not allow collection and use of such signals, then the user may not receive the benefits of the techniques described herein. The user can also be provided with tools to revoke or modify consent. In addition, certain information or data can be treated in one or more ways before it is stored or used, so that personally identifiable information is removed. As an example, a computing system can obtain sensor data which can indicate a scan, without identifying any particular user(s) or particular user computing device(s).

With reference now to the figures, example aspects of the present disclosure will be discussed in greater detail.

FIG. 1 depicts an example of a computing device 100. Computing device 100 may be any mobile or non-mobile computing device. As a mobile computing device, the computing device 100 can be a mobile phone, a laptop computer, a wearable device (e.g., watches, eyeglasses, headphones, clothing), a tablet device, an automotive/vehicular device, a portable gaming device, an electronic reader device, or a remote-control device, or other mobile computing device including a skin diagnostic system 104. As a non-mobile computing device, the computing device 100 may represent a server, a network terminal device, a desktop computer, a television device, a display device, an entertainment set-top device, a streaming media device, a tabletop assistant device, a non-portable gaming device, business conferencing equipment, a payment station, a security checkpoint system, or other non-mobile computing device including skin diagnostic system 104.

Computing device 100 includes an application 102, skin diagnostic system 104, including a sonic fingerprint sensor 106 and a machine-learned diagnostic system 108. These and other components of computing device 100 are communicatively coupled in various ways, such as through the use of wired and wireless buses and links. Computing device 100 may include additional or fewer components than what is shown in FIG. 1.

The application 102 can interface with skin diagnostic system 104 to provide information and data to and from the skin diagnostic system such as for consumption by user or other systems. In some examples, application 102 can be a secured component of the computing device 100 or an access point to secure information accessible from the computing device 100. The application 102 may include or be part of an operating system. Many other examples of the application 102 exist. The application 102 may execute partially on the computing device 100 and partially in "the cloud" (e.g., on the Internet). For example, the application 102 may provide an interface to an online account, such as through an internet browser or an application programming interface (API).

A computing device (e.g., a user device, a mobile telephone, a tablet computer, a wristwatch) may use a sensor such as an optical fingerprint sensor or ultrasonic fingerprint sensor to generate a representation such as an image of a fingerprint or an image of another portion of the skin of a user. Sensor 106 can be any sensor able to generate a representation of a fingerprint or other region of the skin of a user, such as by capturing an ultrasonic measurement of a skin region. The sensor 106 may be an optical fingerprint sensor or an ultrasonic fingerprint sensor such as a three-dimensional ultrasonic fingerprint sensor. For ease of description, sensor 106 is generally described as being integrated with a display that presents a graphical user interface (GUI). For example, sensor 106 can be an in-display ultrasonic fingerprint sensor integrated with a touch screen. The GUI may include instructions for the user to follow to use the sensor 106. For example, the GUI may include a target graphical element (e.g., an icon, a designated region) where the user is to position or touch an area to provide the sensor access to a region of their skin.

Machine-learned diagnostic system 108 includes one or more machine-learned models configured to generate inference data indicative of skin conditions in response to input sensor data. For example, sensor data from screening a skin region by an ultrasonic sensor can be provided as input to the one or more machine-learned models. The machine-learned models(s) are trained to generate inferences indicative of skin conditions such as a melanoma associated with a skin region.

Figure 2:
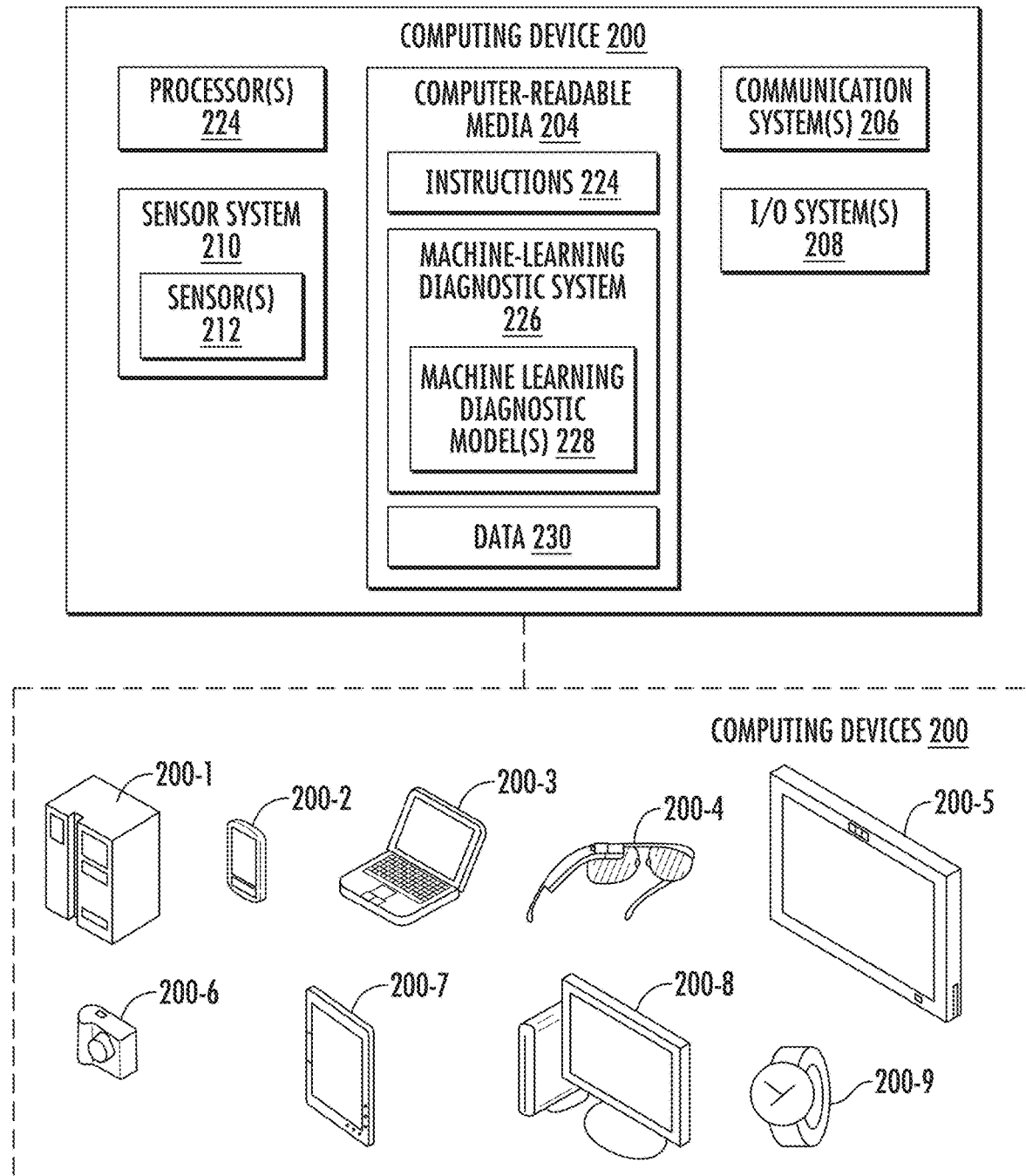
FIG. 2 depicts a block diagram of an example computing device and depicts various implementations of computing devices in accordance with example embodiments of the present disclosure.

FIG. 2 depicts another example computing device 200 such as a user computing device that can serve as a skin condition diagnostic device, such as a skin cancer diagnostic device that utilizes a fingerprint sensor. By way of example, computing device 200 may be a smartphone that includes an in-display ultrasonic fingerprint sensor that can serve as a clinical-grade ultrasonography device using a time-resolved design and machine-learning. Computing devices 200 are illustrated with various non-limiting example devices: server 200-1, smart phone 200-2, laptop 200-3, computing spectacles 200-4, television 200-5, camera 200-6, tablet 200-7, desktop 200-8, and smart watch 200-9, though other devices may also be used, such as home automation and control systems, sound or entertainment systems, home appliances, security systems, netbooks, e-readers, gaming systems or controllers, smart speaker systems, appliances, automobiles, unmanned vehicles (in-air, on the ground, or submersible "drones"), trackpads, drawing pads, netbooks, doorbells, refrigerators, and other devices with a sensor such as an ultrasonic fingerprint sensor.

Note that computing device 200 can be wearable (e.g., computing spectacles and smart watches), non-wearable but mobile (e.g., laptops and tablets), or relatively immobile (e.g., desktops and servers). Computing device 200 may be a local computing device, such as a computing device that can be accessed over a bluetooth connection, near-field communication connection, or other local-network connection. Computing device 200 may be a remote computing device, such as a computing device of a cloud computing system.

Computing device 200 can communicate with other computing devices over one or more networks such as one or more of many types of wireless or partly wireless communication networks, such as a local-area-network (LAN), a wireless local-area-network (WLAN), a personal-area-network (PAN), a wide-area-network (WAN), an intranet, the Internet, a peer-to-peer network, point-to-point network, a mesh network, and so forth.

Computing device 200 includes one or more processors 202, computer-readable media 204, sensor system(s) 210, communication system(s) 206, and input output (I/O) system(s) 208. Processor(s) 202 may include any combination of one or more controllers, microcontrollers, processors, microprocessors, hardware processors, hardware processing units, digital-signal-processors, graphics processors, graphics processing units, and the like. The processors 202 may be an integrated processor and memory subsystem (e.g., implemented as a "system-on-chip"), which processes computer-executable instructions to control operations of the computing device 200. The processors can be any suitable processing device (e.g., a processor core, a microprocessor, an ASIC, a FPGA, a controller, a microcontroller, etc.) and can be one processor or a plurality of processors that are operatively connected. The computer-readable media can include one or more non-transitory computer-readable storage media, such as RAM, ROM, EEPROM, EPROM, flash memory devices, magnetic disks, etc., and combinations thereof. The computer processors 202 and the computer-readable media 204 can include memory media and storage media.

The memory can store instructions 224 (e.g., one or more applications), at least a portion of machine-learning diagnostic system 226, and data 230. Instructions 224 are executed by the processor 202 to cause the computing device 200 to perform operations. Machine-learning diagnostic system 226 can include one or more machine-learned diagnostic models 228. Machine-learning diagnostic system 226 is one example of machine-learned diagnostic system 108. Computer-readable media 204 can include any computer-readable media and can be configured as persistent and non-persistent storage of executable instructions (e.g., firmware, software, applications, modules, programs, functions) and data (e.g., user data, operational data, online data) to support execution of the executable instructions. Examples of the computer-readable media 204 include volatile memory and non-volatile memory, fixed and removable media devices, and any suitable memory device or electronic data storage that maintains executable instructions and supporting data. The computer-readable media 204 can include various implementations of random-access memory (RAM), read-only memory (ROM), flash memory, and other types of storage memory in various memory device configurations. The computer-readable media 204 may be a solid-state drive (SSD) or a hard disk drive (HDD).

Communication system(s) 206 can include various connections and/or interfaces. For example, communication system(s) 206 can include bluetooth connections, near-field communication connections, or other local-network connections, for example. Communication system(s) 206 can communicate using one or more networks such as wireless or partly wireless communication networks, such as a local-area-network (LAN), a wireless local-area-network (WLAN), a personal-area-network (PAN), a wide-area-network (WAN), an intranet, the Internet, a peer-to-peer network, point-to-point network, a mesh network, and so forth.

Input/output (I/O) components 208 can operate as an input device and/or an output device, for example, presenting a GUI and receiving inputs directed to the GUI. Other programs, services, and applications (not shown) can be implemented as computer-readable instructions on the computer-readable media 204, which can be executed by the computer processors 202 to provide functionalities described herein. Fingerprint sensor 212 is included as one of the sensors of sensor system 210. Fingerprint sensor 212 is one example of a fingerprint sensor 106.

The communication system(s) 206 and/or I/O system(s) can provide connectivity to the computing device 200 and other devices and peripherals. The communication and I/O components can include data network interfaces that provide connection and/or communication links between the device and other data networks, devices, or remote systems (e.g., servers). The communication and/or I/O components couple the computing device 200 to a variety of different types of components, peripherals, or accessory devices. Data input ports of the communication and/or I/O components receive data, including image data, user inputs, communication data, audio data, video data, and the like. The communication and/or I/O components enable wired or wireless communicating of device data between the computing device 200 and other devices, computing systems, and networks. Transceivers of the communication and/or I/O components enable cellular phone communication and other types of network data communication.

In addition to fingerprint sensor 212, the sensor system 210 can include other sensors for obtaining contextual information (e.g., sensor data) indicative of operating conditions (virtual or physical) of the computing device 200 or the surroundings of the computing device. The computing device 200 monitors the operating conditions based in part on sensor data generated by the sensor system 210. In addition to the examples given for the sensor 212 to detect fingerprints, other examples of the sensor components include various types of cameras (e.g., optical, infrared), radar sensors, inertial measurement units, movement sensors, temperature sensors, position sensors, proximity sensors, light sensors, infrared sensors, moisture sensors, pressure sensors, and the like.

Melanoma, a type of skin cancer, is known to be one of the most unpredictable tumors, because of its high variability in morphology. In some cases, even experienced dermatologists can give conflicting diagnostics results based on visual analysis of skin lesion surface (reference). Thus, medical imaging tools such as optical coherence tomography (OCT) or ultrasonography, that perform in vivo imaging of below the dermis layer to clearly differentiate skin cancer from other non-malignant conditions is helpful. However, these tools are not readily available to the average consumer for easy check-ups to take early preventive action.

In accordance with example embodiments of the disclosed technology, a computing device is provided, such as a smartphone having a 3D ultrasonic fingerprint sensor that is converted into a clinical-grade ultrasonography device using novel time-resolved system design and machine learning. In accordance with example embodiments, a smartphone can be converted into a skin cancer diagnostic device that can fit in a pocket, for example.

Figure 3:
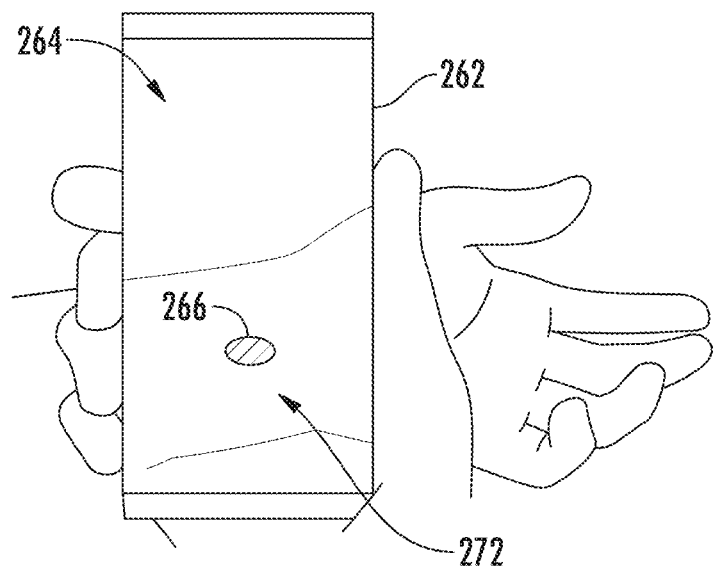
FIG. 3 depicts a block diagram illustrating a user scanning a skin region using a sonic sensor of a user computing device in accordance with example embodiments of the present disclosure.

FIG. 3 depicts an example embodiment of using a computing device 262 such as a user computing device that can serve as diagnostic device, such as a skin condition diagnostic device that utilizes a fingerprint sensor. The user computing device including the fingerprint sensor can be utilized to scan a candidate skin lesion 266, located on the skin region of the user, for skin cancer such as melanoma. The resulting sonic measurement data can be utilized in combination with machine learning techniques to provide accurate diagnostics of skin conditions such as skin cancer. The 3D volumetric sonic data can be provided as input to one or more machine-learned models configured to identify one or more skin cancer conditions based on 3D volumetric sonic data.

Figure 4:
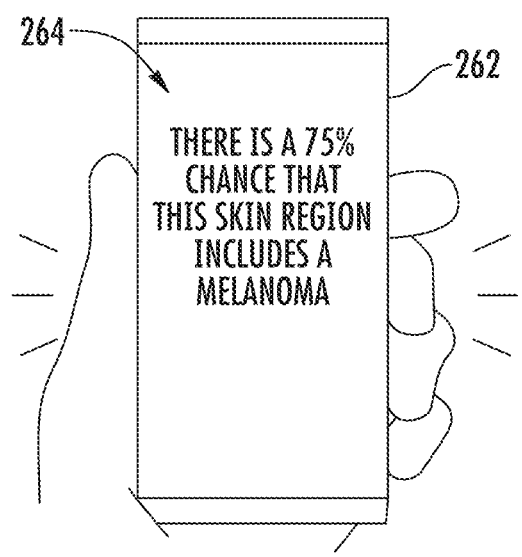
FIG. 4 depicts a block diagram of a user computing device providing an output including a skin condition identification associated with a skin region of a user in accordance with example embodiments of the present disclosure.

FIG. 4 depicts an example embodiment of a computing device 200 such as a user computing device to display outputs of the diagnostic system. More specifically, a computing device 262 such as a smartphone may be used to display, on a display of the computing device 262, the output of the skin cancer condition identification associated with the candidate skin lesion located on the skin region of the user. In one example embodiment, the output of the skin cancer condition is determined using a machine learning diagnostic system. By way of example, the machine-learning diagnostic system can provide an output indicative of one or more skin cancer features from the dictionary that were the basis for the diagnosis. In this manner, a clinician such as a doctor or other professional may assess the process by which the system generated diagnostic data. Such an approach can enable a clinical and technical evaluation of the output that may be useful in a final determination by the clinician making an assessment.

Figure 5:
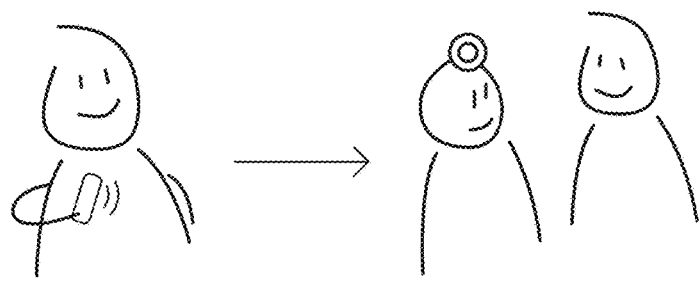
FIG. 5 depicts an example user flow of scanning a candidate skin region using a computing device and visiting a dermatologist in response to a screening that results in positive skin condition identification in accordance with example embodiments of the present disclosure.

FIG. 5 depicts an example user flow where a user scans a candidate skin lesion using a smartphone and visits a dermatologist when a skin diagnostic system in accordance with example embodiments screens a positive result for further analysis.

Figure 6:
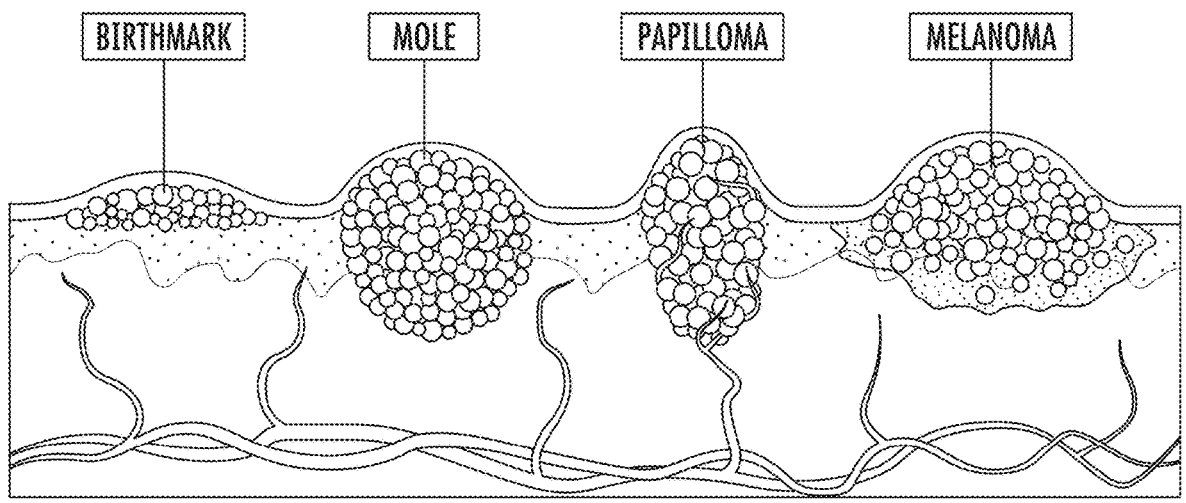
FIG. 6 depicts examples of skin conditions including a birthmark, a mole, a papilloma, and a melanoma.

A large differentiating physiological factor between melanoma and non-malignant conditions such as birthmarks or moles is the increasing volume in depth. FIG. 6 depicts examples including a birthmark, a mole, a papiloma, and a melanoma. As illustrated in FIG. 6, different skin conditions may appear similar at the skin surface but may be differentiated by their depth in the skin and the volume density associated with such depth.

Figure 7:
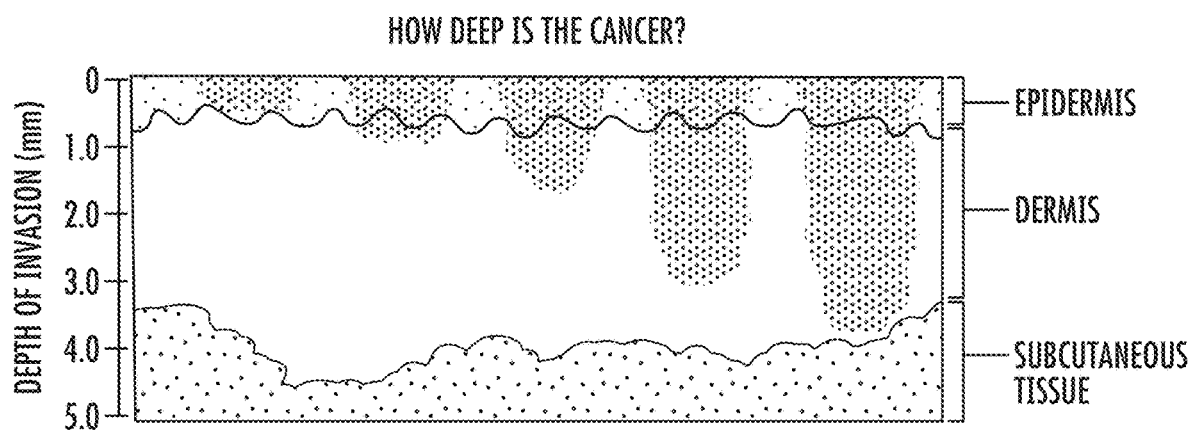

FIG. 7 depicts a diagram where the skin cancer penetrates dermal layers over time while the surface characteristics can more or less look the same. Thus, imaging technologies that can view the inside of the epidermal/dermal layer such as ultrasonography, which is a method of using ultrasonic pulses to resolve volume density, may have higher clinical accuracy than simple surface imagers such as taking camera photos of skin.

Figure 8:
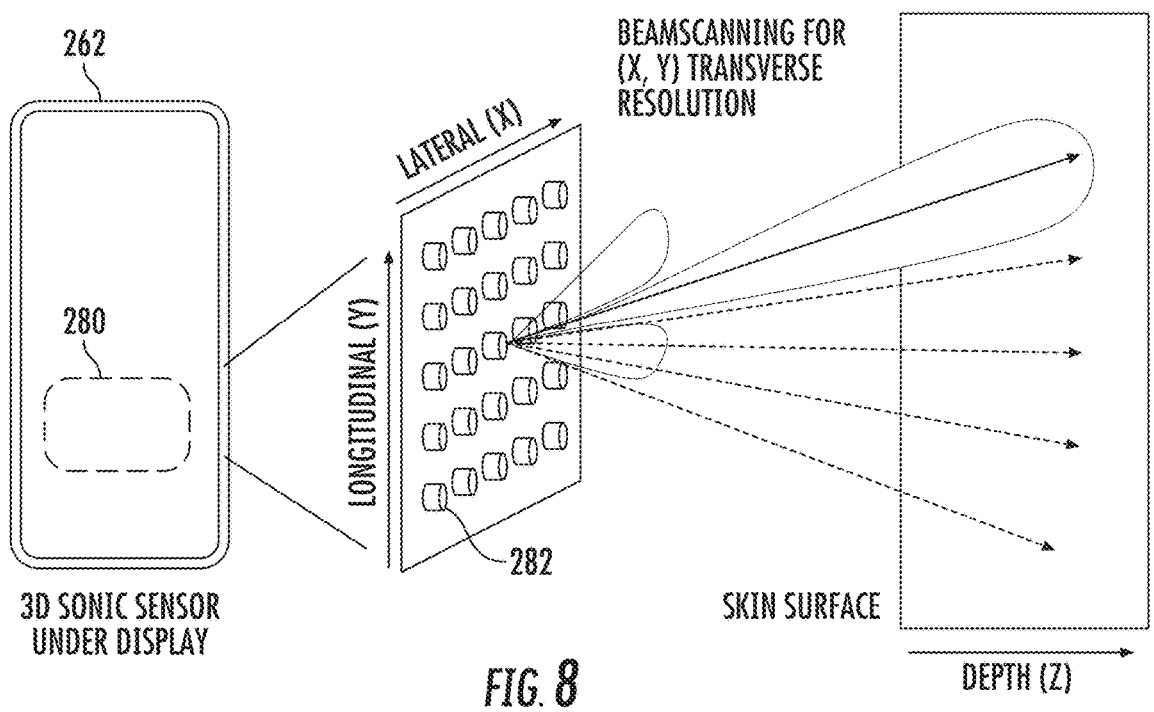
FIG. 8 depicts a block diagram of an example computing device including a three-dimensional (3D) sonic sensor in accordance with embodiments of the present disclosure.

FIG. 8 depicts an example of a computing device 262 that includes a three-dimensional (3D) ultrasonic sensor 280 located under the display of the computing device. The 3D ultrasonic sensor on a smartphone, for example, can be used to sense fingerprints for user authentication. The smartphone can authenticate a user via a fingerprint scan of a first skin region of the user using the three-dimensional sonic sensor of the user computing device. In example embodiments during authentication, the system generates two-dimensional ultrasonic measurement data based at least in part on back-reflection associated with one or more ultrasonic pulses contacting an outer surface of the skin of the user while ignoring time-resolution of back-reflection associated with sub-surface scattering.

As described herein, a three-dimensional sonic sensor located under the display of a computing device such as a smartphone in accordance with example embodiments can be used to generate a representation of a skin region of a user that can be used for diagnostic analysis. In FIG. 8, the 3D ultrasonic sensor can use MHz-operating ultrasonic waves to resolve the valleys of the finger. By way of example, the 3D ultrasonic sensor may operate at 50 MHz in example embodiments. Other operating frequencies may be used.

The 3D ultrasonic sensor 280 may be formed on a chip with an array structure of transducers 282. In the example of FIG. 8, a 5×5 array of 25 transducers is used but any number of transducers may be used. Typically, the number of transducers is less than that of a clinical grade device.

Beamforming such as beamscanning can be used to either beamscan in the analog or digital domain. Beamscanning can be used to increase the transverse resolution in the x (lateral) and y (longitudinal) dimensions. The ultrasonic sensor can form a fingerprint imager that can then be used as a feature to cluster different users in example embodiments. The sonic sensor can operate at higher frequencies such as at or greater than 6 MHz in some examples, at or greater than 50 MHz in some examples, and/or at or greater than 100 MHz in some examples. Higher frequency ranges may be used to provide higher resolution imaging in example embodiments. For instance, at higher frequencies the half wavelength may apply so that transducers can be spaced closely together (e.g., by half the wavelength). The beam can be steered to locations between adjacent transducers to increase resolution. In example, embodiments, the sensor generates two-dimensional ultrasonic measurement data based at least in part on back-reflection associated with one or more ultrasonic pulses contacting an outer surface of the skin of the user.

According to example aspects of the present disclosure, the system of FIG. 8 provides a design with fast analog to digital conversion (ADC) per receive transducer in the array. In this manner, the back-reflected ultrasonic pulses can also be time-resolved to provide depth information in a third-dimension (z-direction). The system can generate depth ultrasonic measurement data based at least in part on time-resolving back-reflection associated with sub-surface scattering of one or more ultrasonic pulses entering a below-surface region of the second skin region of the user.

Figure 9:
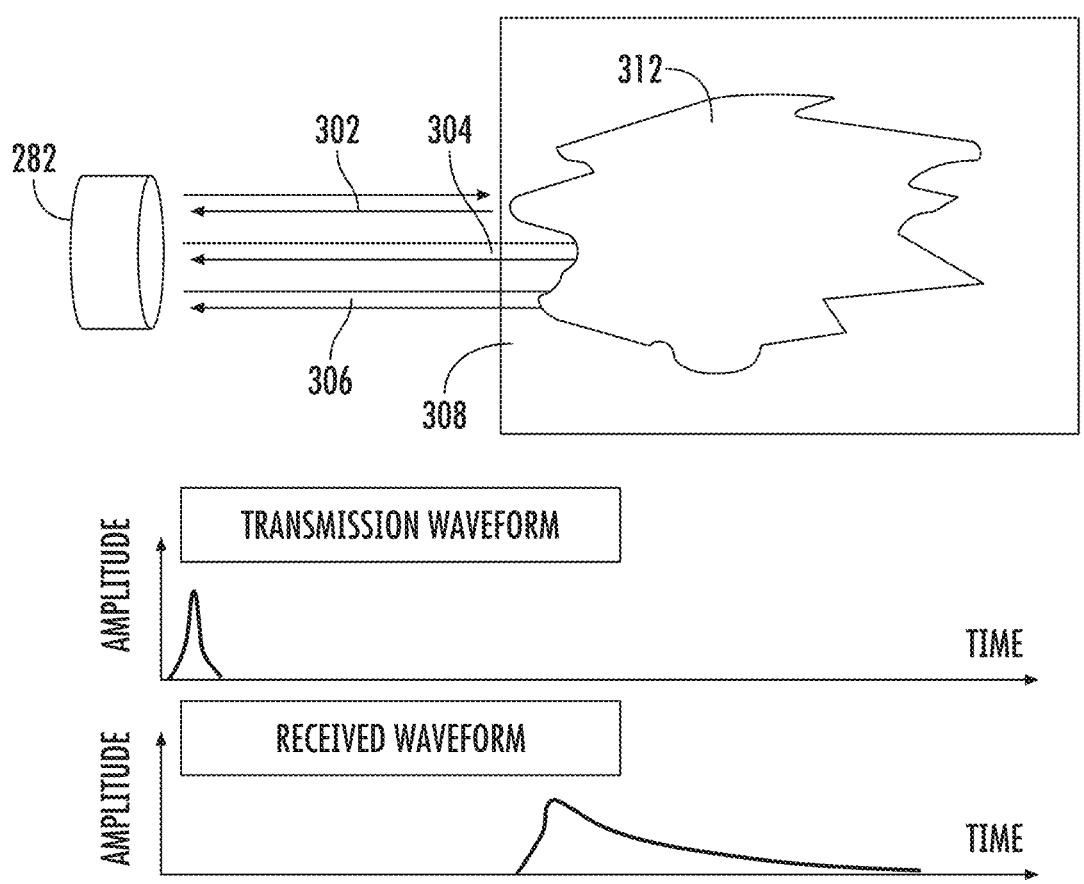
FIG. 9 depicts a simplified illustration of a sonic sensor including a single-transducer and the emission and detection of ultrasonic pulses in accordance with example embodiments of the present disclosure.

FIG. 9 depicts a simple illustration of a the single-transducer case that can be observed as a motivating example. A narrow ultrasonic pulse (e.g., pulse 302) travels to the skin surface, and hits the outer surface first. The skin surface is a first target that provides the back-reflection as illustrated. However, due to MHz skin penetration properties, one or more other pulses such as pulse 304, pulse 306, and/or a sub-pulse of the original pulse enters the below-surface region and generates sub-surface scattering. As shown in the graphs of FIG. 9, the received waveform is shifted in time from the transmission waveform due to the distance traveled in the z-direction. Due to the sub-surface scattering, the received waveform in time is thus not simply a time-shifted version of the original waveform. Rather it is the integral energy of pulses that are back-reflected at epidermal/dermal layers below the surface, such as every epidermal/dermal layer.

As noted above, during fingerprint scanning for authentication, the fingerprinting application does not necessarily need depth information as the high-resolution finger ridges-and-valleys are captured just from the surface and the time-resolution is simply ignored and a time-sum response may be observed instead.

In accordance with example embodiments of the present disclosure, the time-resolving property can be utilized. For skin cancer screening by the skin diagnostic system, a 3D volumetric ultrasonic measurement is provided where the three dimensions are x, y, z in the physical space. The x, y resolution may come from the beamscanning principles and the z resolution come from the back-reflected timing information converted into distance by scaling. For example, the timing information can be converted into distance by scaling by the speed of sound. The timing can be scaled based on the speed of sound, such as by scaling by the speed_of_sound/2 (the factor of 2 is included because of the pulse round trip).

Figure 10:
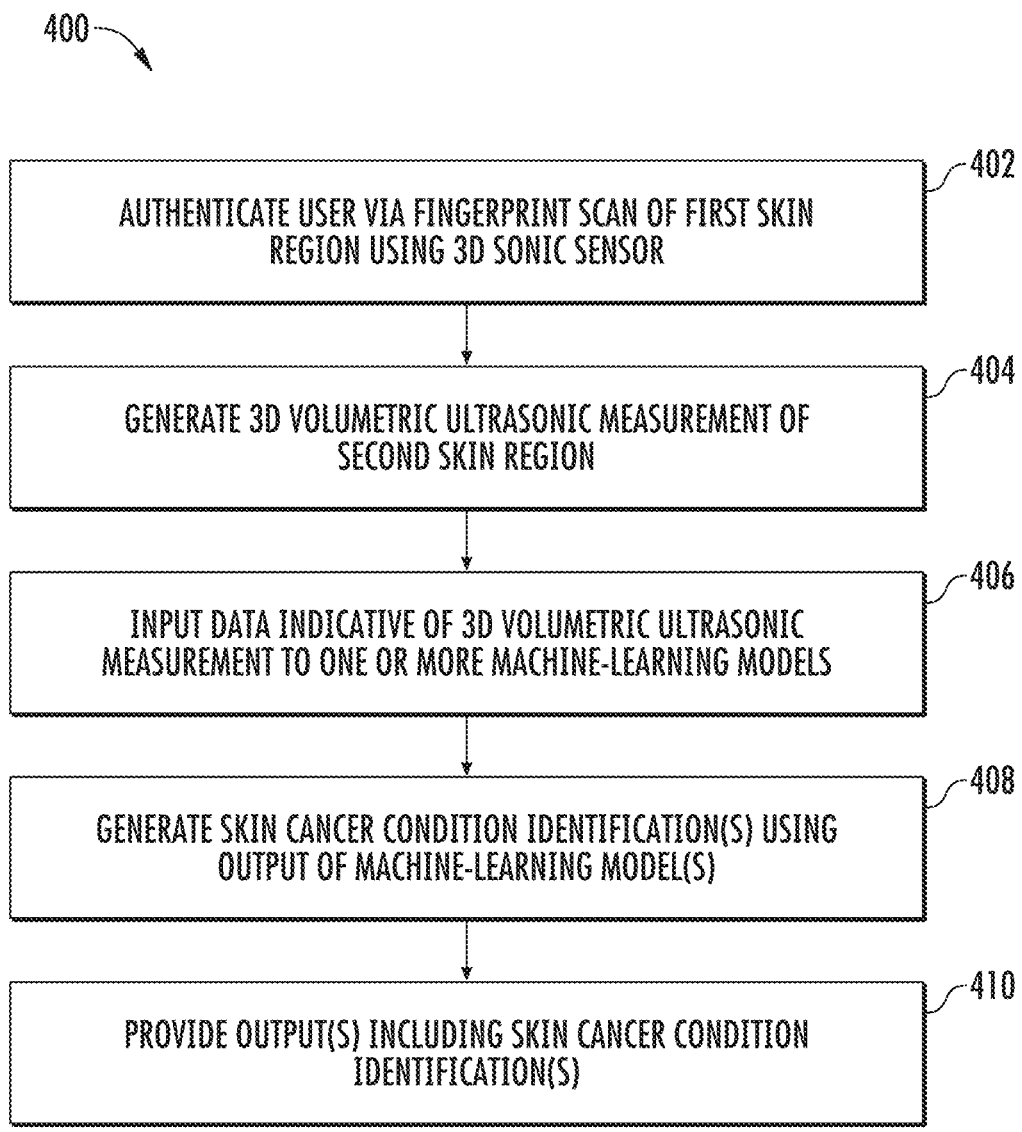
FIG. 10 is a flowchart depicting an example process of generating skin condition identifications associated with a skin region of a user in accordance with example embodiments of the present disclosure.

FIG. 10 illustrates an example method 400 of processing sensor data to generate skin condition identifications associated with a skin region of the user. This method and other methods herein are shown as sets of blocks that specify operations performed but are not necessarily limited to the order or combinations shown for performing the operations by the respective blocks. One or more portions of method 400, and the other processes described herein (e.g., method 420, method 600, and/or method 800), can be implemented by one or more computing devices such as, for example, one or more computing devices of a computing environment as illustrated in FIG. 1, 2, 17, 18, or 19. While in portions of the following discussion reference may be made to a particular computing environment, reference to which is made for example only. The techniques are not limited to performance by one entity or multiple entities operating on one device. One or more portions of these processes can be implemented as an algorithm on the hardware components of the devices described herein.

At 402, method 400 can include authenticating a user via a fingerprint scan of a first skin region of the user using a three-dimensional (3D) sonic sensor of the user computing device. The 3D ultrasonic sensor on a smartphone, for example, can be used to sense fingerprints for user authentication. The smartphone can authenticate a user via a fingerprint scan of a first skin region of the user using the three-dimensional sonic sensor of the user computing device. In example embodiments during authentication, the system generates two-dimensional ultrasonic measurement data based at least in part on back-reflection associated with one or more ultrasonic pulses contacting an outer surface of the skin of the user while ignoring time-resolution of back-reflection associated with sub-surface scattering.

At 404, a three-dimensional (3D) volumetric ultrasonic measurement of a second skin region is generated by the one or more processors of the user computing device. The three-dimensional (3D) volumetric ultrasonic measurement may be based at least in part on data obtained by the three-dimensional (3D) sonic sensor e.g. (one or more ultrasonic pulses of the three-dimensional (3D) sonic sensor). Back-reflection of sonic pulses at the outer surface of the skin can be measured to generate lateral data (e.g., x-direction) and longitudinal data (e.g., y-direction) indicative of skin features at the outer surface of the user's skin. A pulse entering the below-surface region of the user's skin results in sub-surface scattering. Back-reflection of the pulse entering the below-surface region can be measured to generate depth data indicative of skin features in the below-surface region of the user's skin. The received waveform(s) that result from the backscattering can be time resolved to determine depth data associated with the surface skin features.

At 406, data indicative of the three-dimensional (3D) volumetric ultrasonic measurement is input into one or more machine-learning models. The one or more machine-learning models may be configured to identify one or more skin cancer conditions in response to one or more 3D volumetric measurement inputs. The machine-learned model(s) may be configured to enforce an optimization using a dictionary of skin cancer features in example embodiments. In another example, the machine-learned model(s) may operate without a dictionary. For example, a model may be trained to generate classifications or detections based on raw input data.

At 408, one or more skin condition identifications associated with the second skin region of the user are generated based at least in part on one or more outputs of the one or more machine-learning models. For example, the machine-learning system may identify one or more skin cancer features in the dictionary for which a convergence rule is met after computing a gradient descent on a data loss term when comparing the dictionary feature(s) and the input data.

At 410, one or more outputs including the skin condition identifications associated with the second skin region of the user are provided. By way of example, the output(s) may include audio, visual, or other outputs to indicate an assessment of the second skin region. For instance, an application on a smartphone or other device may generate a graphical user interface with a display of the one or more skin cancer identifications. In some examples, the system may provide a confidence score such as a probability associated with one or more skin condition identification. In performing optimization, the model can compute an error between a dictionary feature and the input data. The error associated with the matching feature can be indicative of the confidence. For example, the confidence can be the inverse of the error in example embodiments.

Figure 11:
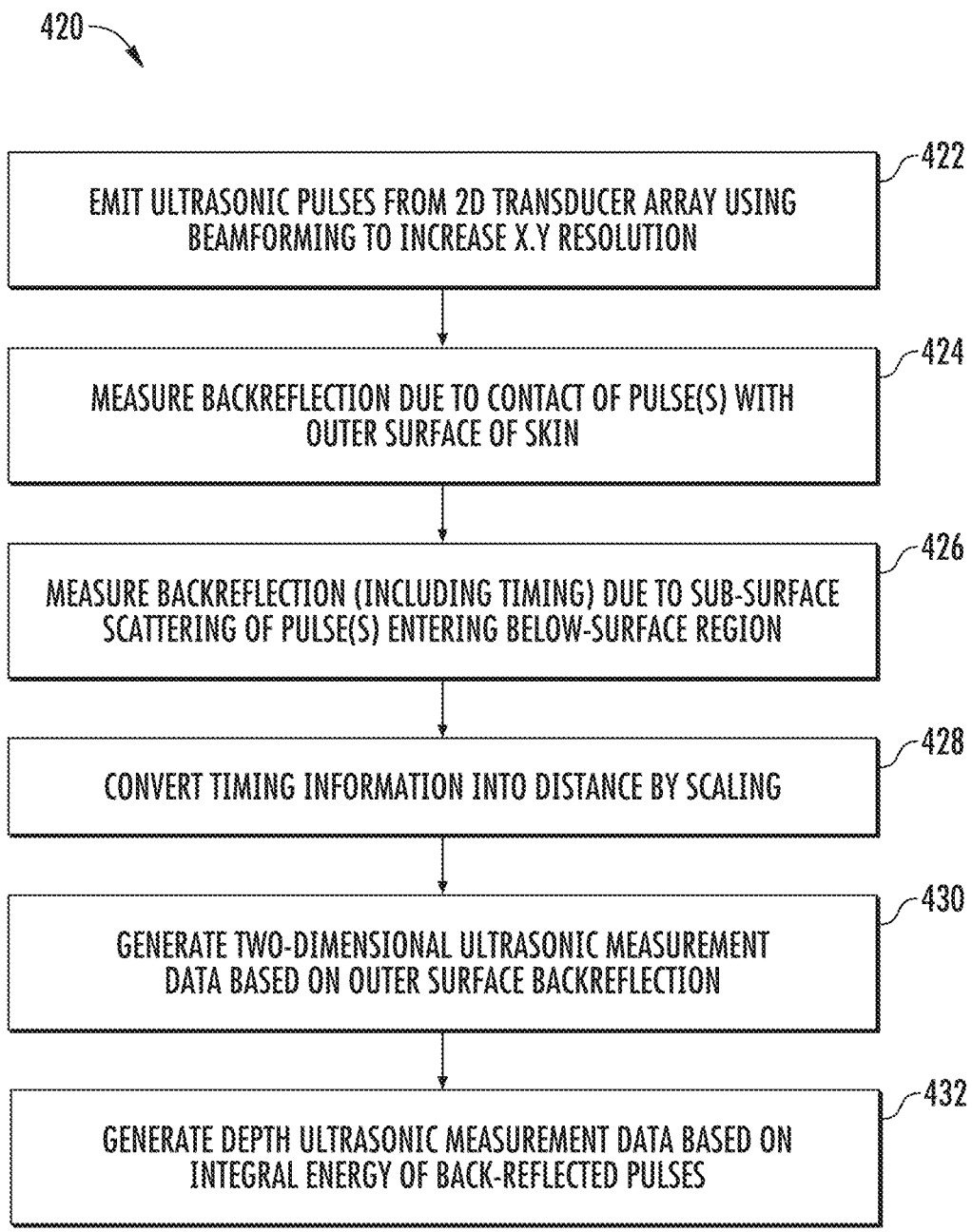
FIG. 11 is a flowchart depicting an example process of generating three-dimensional ultrasonic measurement data based on back-reflection associated with one or more ultrasonic pulses in accordance with example embodiments of the present disclosure.

FIG. 11 illustrates an example method 420 of generating three-dimensional (3D) ultrasonic measurement data based on back-reflection associated with one or more ultrasonic pulses. Method 420 is one example of a generating 3D volumetric ultrasonic measurement data at 404 of FIG. 10.

At 422, one or more ultrasonic pulses are emitted from a two-dimensional transducer array. The pulse transmitted by the two-dimensional transducer array may be steered e.g. (beamsteering) to increase the longitudinal (y) and lateral (x) resolution of the two-dimensional array. The one or more ultrasonic pulses contact the outer surface of the skin of the user, returning back-reflection to the transducer. The back-reflection may comprise data associated with one or more ultrasonic pulses contacting an outer surface of the skin of the user as well as data associated with sub-surface scattering of one or more ultrasonic pulses entering the below-surface region of the skin region.

At 424, back-reflection associated with one or more ultrasonic pulses contacting an outer surface of the skin of the user is measured to generate two-dimensional ultrasonic measurement data.

At 426, method 420 can include measuring back-reflection due to sub-surface scattering of pulse(s) entering a below-surface region of the skin. At 426, time-resolution of the back-reflection associated with sub-surface scattering of one or more ultrasonic pulses entering the below-surface region of the skin region can be measured to generate depth ultrasonic measurement data. The received waveform(s) that result from the backscattering can be time resolved to determine depth data associated with the surface skin features. Moreover, the received waveform is the integral energy of pulses that are backreflected at one or more epidermal and/or dermal layers below the outer surface. Thus, the received waveform is not simply a time-shifted version of the original waveform. Rather, its integral energy is indicative of the sub-surface skin properties.

At 428, method 420 can include converting the back-reflected timing information into distance based on scaling by the speed of sound.

At 430, method 420 can include generating two-dimensional ultrasonic measurement data based on the outer surface back-reflection measured at 424. At 432, method 420 can include generating depth ultrasonic measurement data based on the integral energy of the back-reflected pulses as measured at 426 and time resolved at 428.

Figure 12:
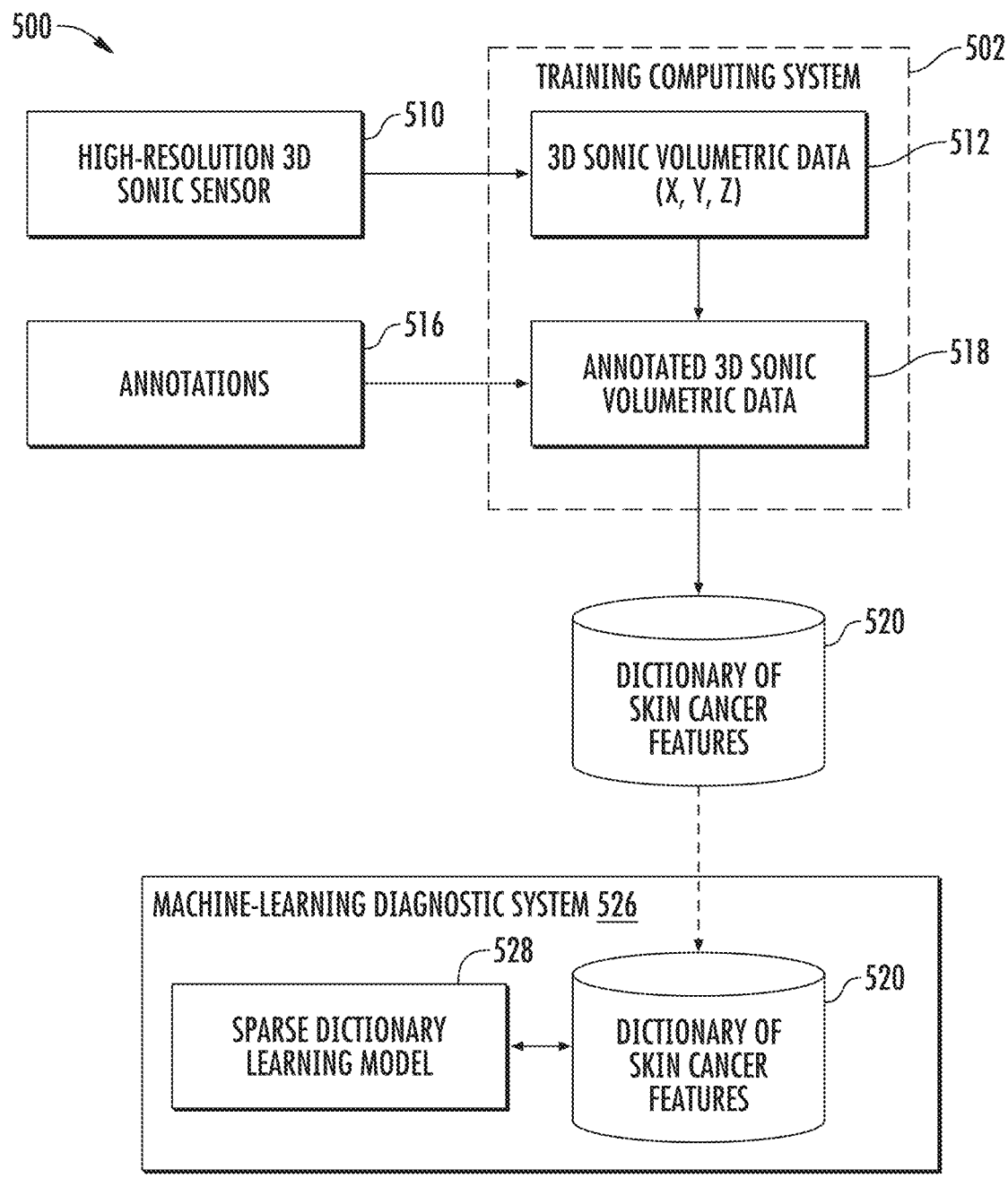
FIG. 12 depicts an example of skin regions corresponding to a melanoma and a non-malignant tumor.

FIG. 12 depicts an example of the true regions of a melanoma and a non-malignant tumor. FIG. 12 also depicts the melanoma and the non-malignant tumor as the volumetric data observed by a three-dimensional sonic sensor. A voxel blurring phenomenon occurs because of the non-linear sub-surface ultrasonic scattering. A widened, dispersion-suffering pulse can be observed. This observation is illustrated above with simulated data where each column is a measurement over depth and the dotted line is skin lesion location as reference. The raw observed data may include blurring that provides very little visual separation between melanoma and non-melanoma when compared to the true representation where it can be observed that there is an increased depth of feature which is a strong cue for diagnostics.

In accordance with example embodiments, a technical approach is provided including sparse dictionary learning (SDL) of skin cancer responses. In order to resolve original skin cancer cell regions from observations, the skin diagnostic system can solve what can be phrased as a voxel-deblurring problem. In accordance with example embodiments, a novel sparse dictionary learning approach is provided. This approach includes a machine learning approach where a dictionary of melanoma features is constructed in a 3D sonic sensing image domain. The system enforces an optimization problem to find the representation that gives the best fit to this dictionary. The optimization can be structured as a minimization shown below.

$$\text{minimize } \Sigma_{k=1}^{n} \|h(X_k) - Y_k\|_2^2 + \lambda \|X_k\|_1$$

The algorithm to solve the above optimization with deterministic convergence guarantees can be an iterative shrinkage thresholding (ISTA) method in example embodiments. The above minimization is determined as a comparison of the input data Y and the dictionary X of skin cancer features x.

An example of the ISTA method in accordance with example embodiments an include computing a gradient descent on the data loss term as shown below for each skin cancer feature x in the dictionary when compared with the input data Y.

$$\nabla x_k = h(h(X_k) - Y_k))$$

$$X_k \leftarrow X_k - \alpha \nabla x_k$$

A proximal map can be computed as shown below followed by iterating the computation of the gradient descent and the proximal computation until a convergence rule is met. The convergence rule is a predetermined convergence rule in example embodiments.

$$X_k \leftarrow \max(X_k - \lambda, 0)$$

Figure 13:
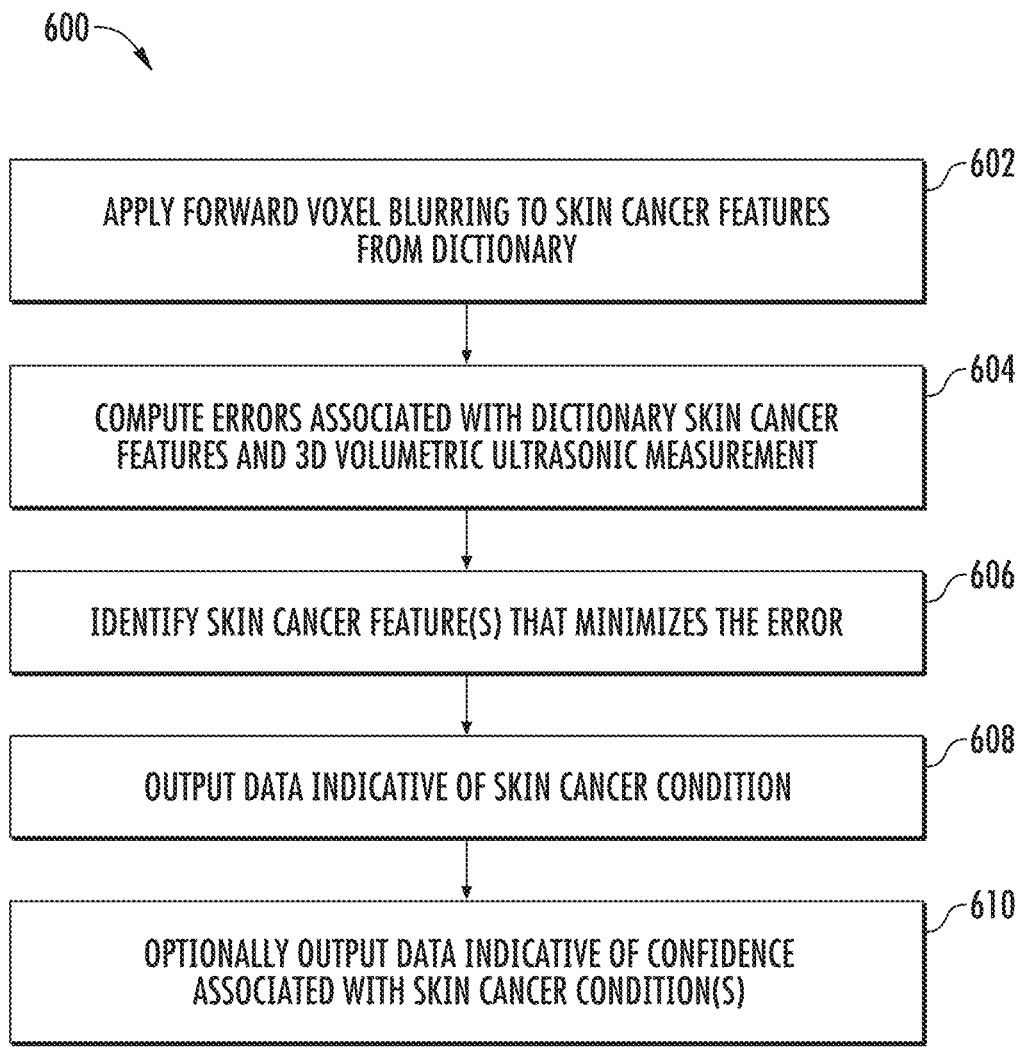
FIG. 13 depicts a block diagram of an example computing system for training and deploying a machine-learned model in accordance with example embodiments of the present disclosure.

FIG. 13 depicts a block diagram of an example computing system for training and deploying a machine-learned model in accordance with example embodiments of the present disclosure. A sparse dictionary learning approach is provided that enables a consumer-level computing device to generate diagnostics whose logic and process can be observable by a clinician. A dictionary 520 of skin cancer or other features can be constructed in a three-dimensional sonic sensing domain and an optimization problem can be enforced using machine-learning to find a representation in the dictionary that best matches or fits to input volumetric ultrasonic data. In example embodiments, the dictionary can be constructed using sensor data 510 that is generated using a sonic sensor having a higher resolution than the sonic sensor of the computing device that is used to scan a user. By way of example, the sonic sensor of a computing device such as a smartphone for scanning a user may include an array of tens to thousands of transducers (e.g., 5×5-50×50 arrays) while a laboratory device used to generate the dictionary may include more transducers such as thousands to millions of transducers (e.g., 100×100 array). In this manner, three-dimensional sonic volumetric data 512 can be generated with a more accurate representation of skin cancer features that can be used by the model when comparing to input data. Annotations 516 are applied to the sensor data to generated annotated 3D sonic volumetric data 518. The annotations can be human generated and/or machine-generated in example embodiments. The annotated sensor data 518 is provided as a dictionary 520 of skin cancer features.

The dictionary 520 of skin cancer features can be deployed with a sparse dictionary learning model 528 to form a machine-learning diagnostic system 526. By way of example, the machine-learning diagnostic system can provide an output indicative of one or more skin cancer features from the dictionary that were the basis for the diagnosis. In this manner, a clinician such as a doctor or other professional may assess the process by which the system generated diagnostic data. As such, the clinician not only has access to the final output but also the process and data underlying the diagnostic. Such an approach can enable a clinical and technical evaluation of the output that may be useful in a final determination by the clinician making an assessment.

As an example, the sparse dictionary learning model can be configured to identify a skin condition that best represents or fits with the measurement data generated by a user. The dictionary of skin cancer features a machine learning approach to gather data of melanoma features constructed in a 3D sonic sensing image domain. After deployment, the system can generate a three-dimensional volumetric ultrasonic measurement of a skin region of a user based on ultrasonic pulses of a lower-resolution 3D sonic sensor. The system can input the measurement data into the machine-learned sparse dictionary learning model. The learning model can determine from the dictionary the skin feature that best represents or fits the input data.

Figure 14:
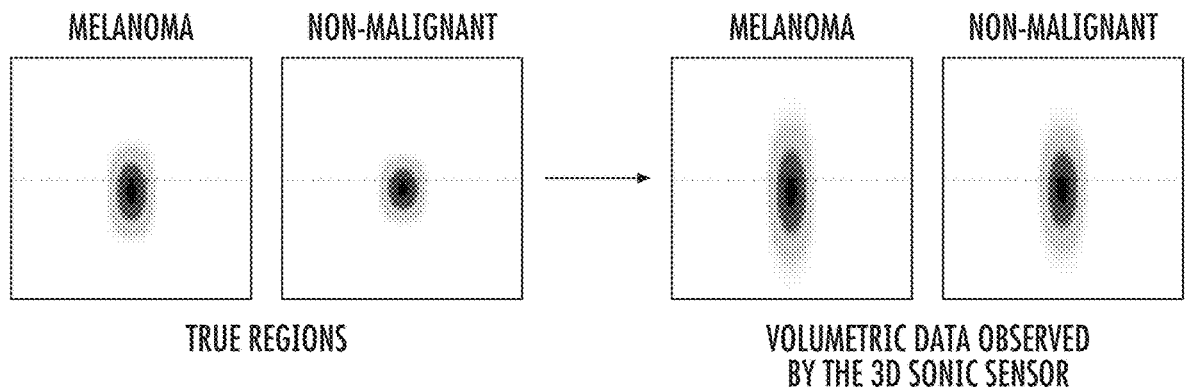
FIG. 14 is a flowchart depicting an example process of identifying features that minimize the error between the data indicative of the 3D volumetric ultrasonic measurement and the dictionary of skin cancer features.

FIG. 14 is a flowchart illustrating an example method 600 of generating one or more outputs of a skin condition diagnostic system in accordance with an example embodiment of the present disclosure. Method 600 is one example of a sparse dictionary learning approach that addresses the voxel blurring phenomena associated with lower resolution sensors.

At 604, method 600 can include computing one or more errors associated with the dictionary skin condition features and the 3D volumetric ultrasonic measurement data generated by the 3D sonic sensor. In an example at 604, method 600 can include computing a gradient descent on a data loss term based on a difference between a dictionary feature and the sonic measurement data. Further, the system can compute a proximal map and iterate until a convergence rule is met.

At 606, method 600 can include identifying one or more skin condition features from the dictionary that minimize the error calculated at 604. At 606, method 600 can include identifying one or more features that result in satisfaction of one or more convergence rules.

At 608, method 600 can include outputting data indicative of one or more skin conditions. Various audio, visual, and/or other outputs may be provided including an indication of a skin cancer identification.

At 610, method 600 can optionally include outputting data indicative of a confidence associated with the skin condition(s). The confidence may be calculated based on an inverse of the error at 604 for the identified skin cancer condition(s).

Figure 15:
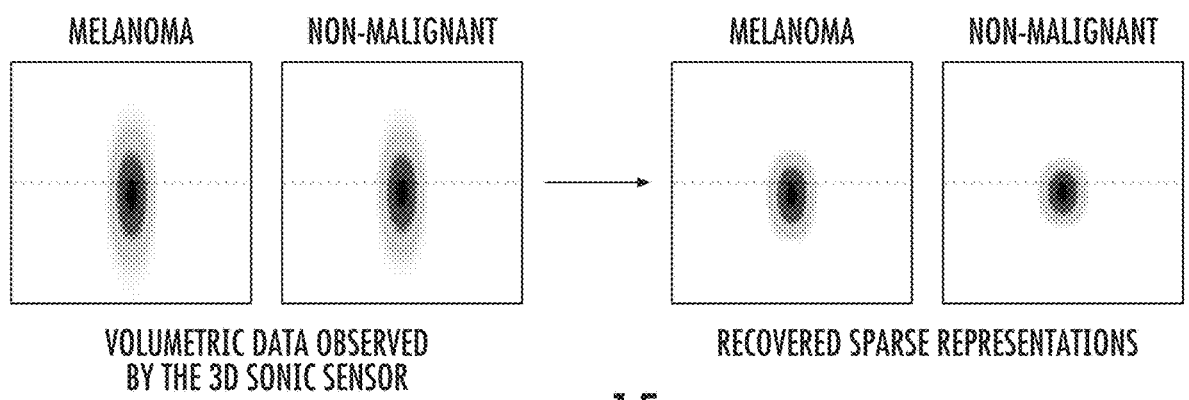
FIG. 15 depicts a sample recovery of true cell volumes from dispersion-corrupted volumetric sonic measurements depicted in FIG. 12.

FIG. 15 depicts a sample recovery of the true cell volumes from the dispersion-corrupted volumetric sonic measurements illustrated in FIG. 12. In FIG. 15, the recovered sparse representations indicate the recovery of the true cell volumes as a result of a sparse dictionary learning approach.

Figure 16:
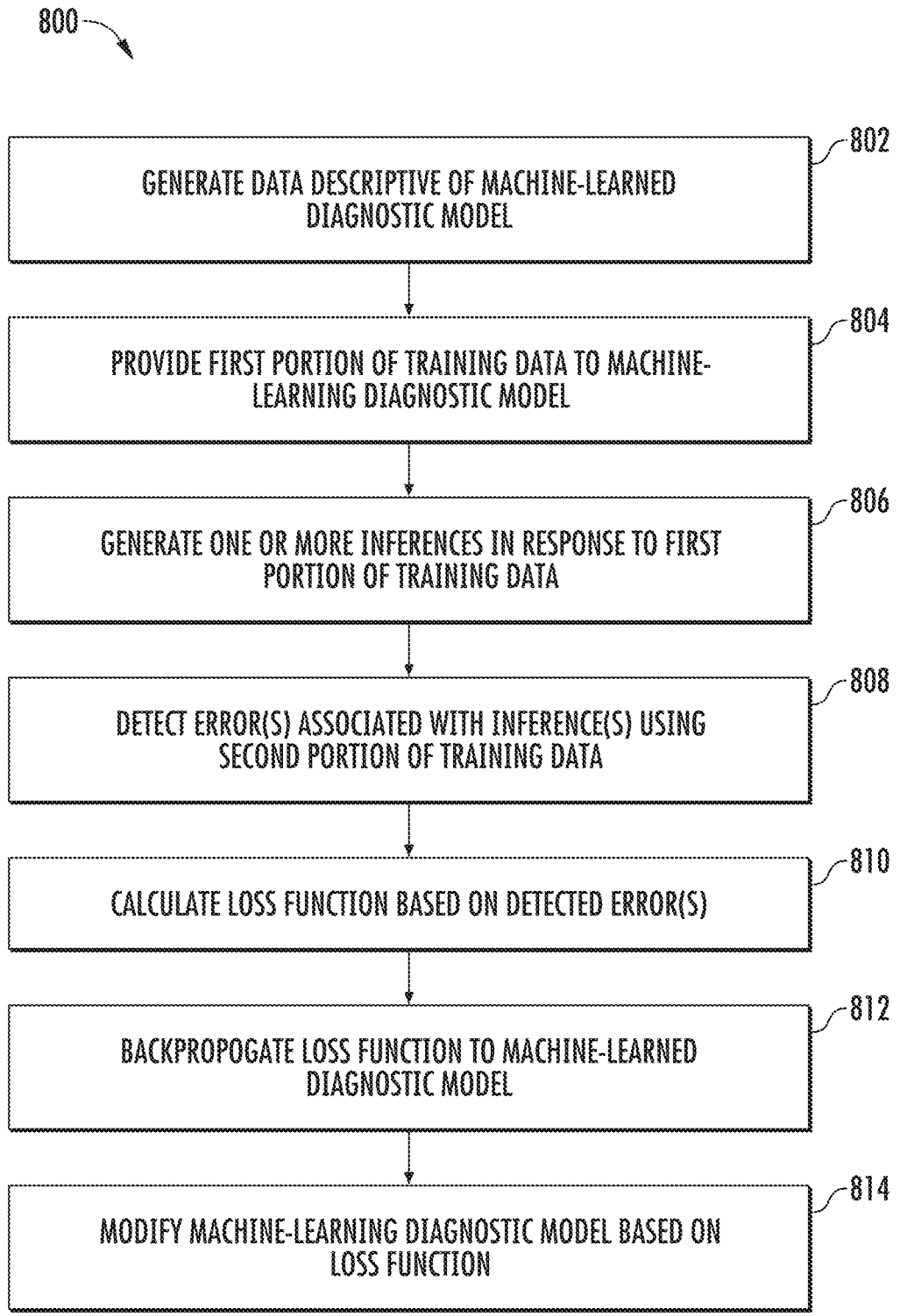
FIG. 16 is a flowchart depicting an example method for training a machine-learned model configured for classification of skin conditions based on 3D volumetric ultrasonic data.

FIG. 16 is a flowchart depicting an example method 800 of training a machine-learned model to generate a diagnostic classification for a skin region of a user based on 3D volumetric sonic sensor data.

At 802, method 800 can include generating data descriptive of a machine-learned diagnostic model. According to some example aspects, an end-to-end machine-learned model is provided that takes as input raw volumetric ultrasonic data and generates as an output one or more indications of skin condition(s). A machine-learned detection or classification approach can be provided to identify skin conditions directly in response to 3D volumetric ultrasonic data in example embodiments. In this example, a dictionary of skin condition features is not necessarily provided. The end-to-end model may operate without an on-device dictionary of skin cancer features.

At 804, method 800 can include providing a first portion of training data to the machine-learned model. The training data may include sensor data and/or feature representation data. The first portion of the training data can include 3D volumetric sonic sensor data generated by a high resolution sensor in example embodiments.

At 806, one or more inferences can be generated by the machine-learned model based on the first portion of the training data. For instance, in response to sensor data, an inference of the presence of a particular skin cancer condition can be generated.

At 808, one or more errors are detected in association with the inferences based on the second portion of the training data. The second portion of the training data can include annotations indicative of a presence or non-presence of a particular skin condition. For example, the model trainer may detect an error between the inference generated by the model and the annotation for the corresponding first portion of the training data.

At 810, method 800 can include calculating one or more loss functions based on the detected errors. In some examples, the loss functions can be based on an overall output of the machine-learned model. The loss function can be applied to the model for modification. In some examples, a loss function may include a sub-gradient.

At 812, method 800 can include backpropagating the one or more loss functions to the model. For example, a sub-gradient calculated for the model can be backpropagated at 812.

At 814, one or more portions of the machine-learned model can be modified based on the backpropagation at 812. In some examples, the machine-learned model may be modified based on backpropagation of the loss function such as a by the sub-gradient.

Figure 17:
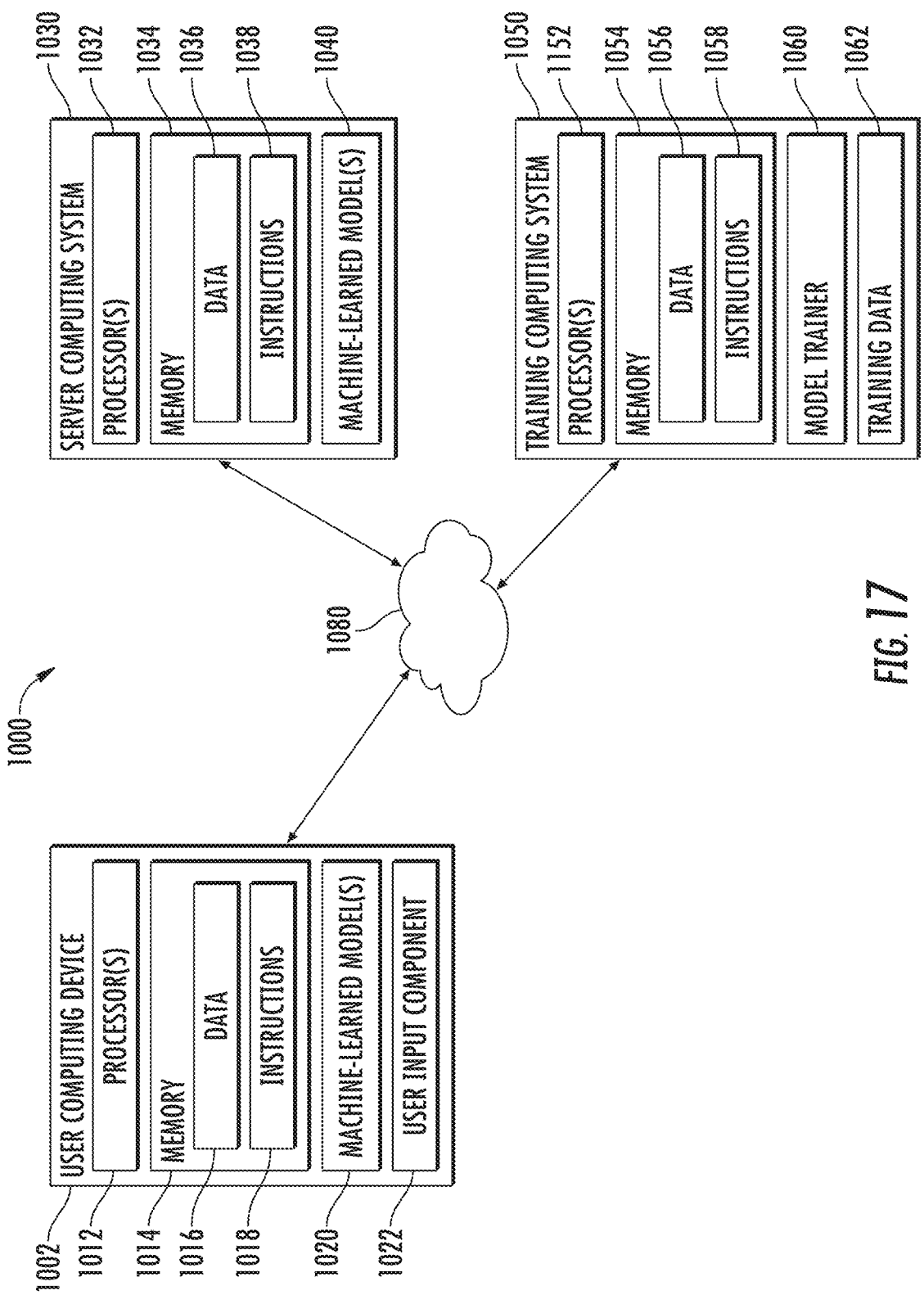
FIG. 17 depicts a block diagram of an example computing system for training and deploying a machine-learned model in accordance with example embodiments of the present disclosure.

FIG. 17 depicts a block diagram of an example computing system 1000 that can be used to implement any of the computing devices described herein. The computing system 1000 can include a user computing device 1002, a server computing system 1030, and/or a training computing system 1050 that are communicatively coupled over a network 1080.

The user computing device 1002 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 1002 includes one or more processors 1012 and a memory 1014. The one or more processors 1012 can be any suitable processing device (e.g., a processor core, a microprocessor, an ASIC, a FPGA, a controller, a microcontroller, etc.) and can be one processor or a plurality of processors that are operatively connected. The memory 1014 can include one or more non-transitory computer-readable storage mediums, such as RAM, ROM, EEPROM, EPROM, flash memory devices, magnetic disks, etc., and combinations thereof. The memory 1014 can store data 1016 and instructions 1018 which are executed by the processor 1012 to cause the user computing device 1002 to perform operations.

The user computing device 1002 can include one or more portions of a machine-learned model 1020. In some implementations, the machine-learned model can store or include one or more portions of a skin condition diagnostic model (e.g., melanoma diagnostic model). For example, the machine-learned model can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks.

In some implementations, the machine-learned model can be received from the server computing system 1030 over network 1080, stored in the user computing device memory 1014, and then used or otherwise implemented by the one or more processors 1012. In some implementations, the user computing device 1002 can implement multiple parallel instances of the machine-learned model (e.g., to perform parallel inference generation across multiple instances of sensor data).

Additionally or alternatively to the machine-learned model 1020, the server computing system 1030 can include one or more machine-learned models 1040. The machine-learned model(s) 1040 can generate data indicative of a skin condition such as a cancer (e.g., melanoma) as described herein.

Additionally or alternatively to the machine learned models 1020, one or more machine learned models 1040 can be included in or otherwise stored and implemented by the server computing system 1030 that communicates with the user computing device 1002 according to a client-server relationship. For example, the machine learned models 1040 can be implemented by the server computing system 1030 as a portion of a web service (e.g., user movement recognition service). Thus, the machine learned models can be stored and implemented at the user computing device 1002 and/or at the server computing system 1030. The one or more machine learned models 1040 can be the same as or similar to the one or more machine learned models 1020.

The user computing device 1002 can also include one or more user input components 1022 that receive user input. For example, the user input component 1022 can be a touch-sensitive component that is sensitive to the touch of a user input object (e.g., a finger or a stylus). The touch-sensitive component can serve to implement a virtual keyboard. Other example user input components include a microphone, a traditional keyboard, or other means by which a user can provide user input.

The server computing system 1030 includes one or more processors 1032 and a memory 1034. The one or more processors 1032 can be any suitable processing device (e.g., a processor core, a microprocessor, an ASIC, a FPGA, a controller, a microcontroller, etc.) and can be one processor or a plurality of processors that are operatively connected. The memory 1034 can include one or more non-transitory computer-readable storage mediums, such as RAM, ROM, EEPROM, EPROM, flash memory devices, magnetic disks, etc., and combinations thereof. The memory 1034 can store data 1036 and instructions 1038 which are executed by the processor 1032 to cause the server computing system 1030 to perform operations.

In some implementations, the server computing system 1030 includes or is otherwise implemented by one or more server computing devices. In instances in which the server computing system 1030 includes plural server computing devices, such server computing devices can operate according to sequential computing architectures, parallel computing architectures, or some combination thereof.

As described above, the server computing system 1030 can store or otherwise include one or more machine learned models 1040. Example machine-learned models include neural networks or other multi-layer non-linear models. Example neural networks include feed forward neural networks, deep neural networks, recurrent neural networks, and convolutional neural networks.

The user computing device 1002 and/or the server computing system 1030 can train the machine learned models 1020 and/or 1040 via interaction with the training computing system 1050 that is communicatively coupled over the network 1080. The training computing system 1050 can be separate from the server computing system 1030 or can be a portion of the server computing system 1030.

The training computing system 1050 includes one or more processors 1052 and a memory 1054. The one or more processors 1052 can be any suitable processing device (e.g., a processor core, a microprocessor, an ASIC, a FPGA, a controller, a microcontroller, etc.) and can be one processor or a plurality of processors that are operatively connected. The memory 1054 can include one or more non-transitory computer-readable storage mediums, such as RAM, ROM, EEPROM, EPROM, flash memory devices, magnetic disks, etc., and combinations thereof. The memory 1054 can store data 1056 and instructions 1058 which are executed by the processor 1052 to cause the training computing system 1050 to perform operations. In some implementations, the training computing system 1050 includes or is otherwise implemented by one or more server computing devices.

The training computing system 1050 can include a model trainer 1060 that trains a machine-learned model stored at the user computing device 1002 and/or the server computing system 1030 using various training or learning techniques, such as, for example, backwards propagation of errors. In other examples as described herein, training computing system 1050 can train a machine-learned model prior to deployment for provisioning of the machine-learned model at user computing device 1002 or server computing system 1030. The machine-learned model can be stored at training computing system 1050 for training and then deployed to user computing device 1002 and server computing system 1030. In some implementations, performing backwards propagation of errors can include performing truncated backpropagation through time. The model trainer 1060 can perform a number of generalization techniques (e.g., weight decays, dropouts, etc.) to improve the generalization capability of the models being trained.

In particular, the model trainer 1060 can train the machine learned models 1020 and 1040 based on a set of training data 1062. The training data 1062 can include, for example, a plurality of instances of sensor data, where each instance of sensor data has been labeled with ground truth inferences such as indications of motion complexity, motion intensity, motion skill, etc. For example, the label(s) for each training data can describe the position and/or movement (e.g., velocity or acceleration) of a touch input or an object movement. In some implementations, the labels can be manually applied to the training data by humans. In some implementations, the models can be trained using a loss function that measures a difference between a predicted inference and a ground-truth inference. In some implementations, the models can be trained using a combined loss function. The total loss can be backpropagated through the model.

In some implementations, if the user has provided consent, the training examples can be provided by the user computing device 1002. Thus, in such implementations, the machine learned model 1020 provided to the user computing device 1002 can be trained by the training computing system 1050 on user-specific data received from the user computing device 1002. In some instances, this process can be referred to as personalizing the model.

The model trainer 1060 includes computer logic utilized to provide desired functionality. The model trainer 1060 can be implemented in hardware, firmware, and/or software controlling a general purpose processor. For example, in some implementations, the model trainer 160 includes program files stored on a storage device, loaded into a memory and executed by one or more processors. In other implementations, the model trainer 1060 includes one or more sets of computer-executable instructions that are stored in a tangible computer-readable storage medium such as RAM hard disk or optical or magnetic media.

The network 1080 can be any type of communications network, such as a local area network (e.g., intranet), wide area network (e.g., Internet), or some combination thereof and can include any number of wired or wireless links. In general, communication over the network 1080 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

Figure 18:
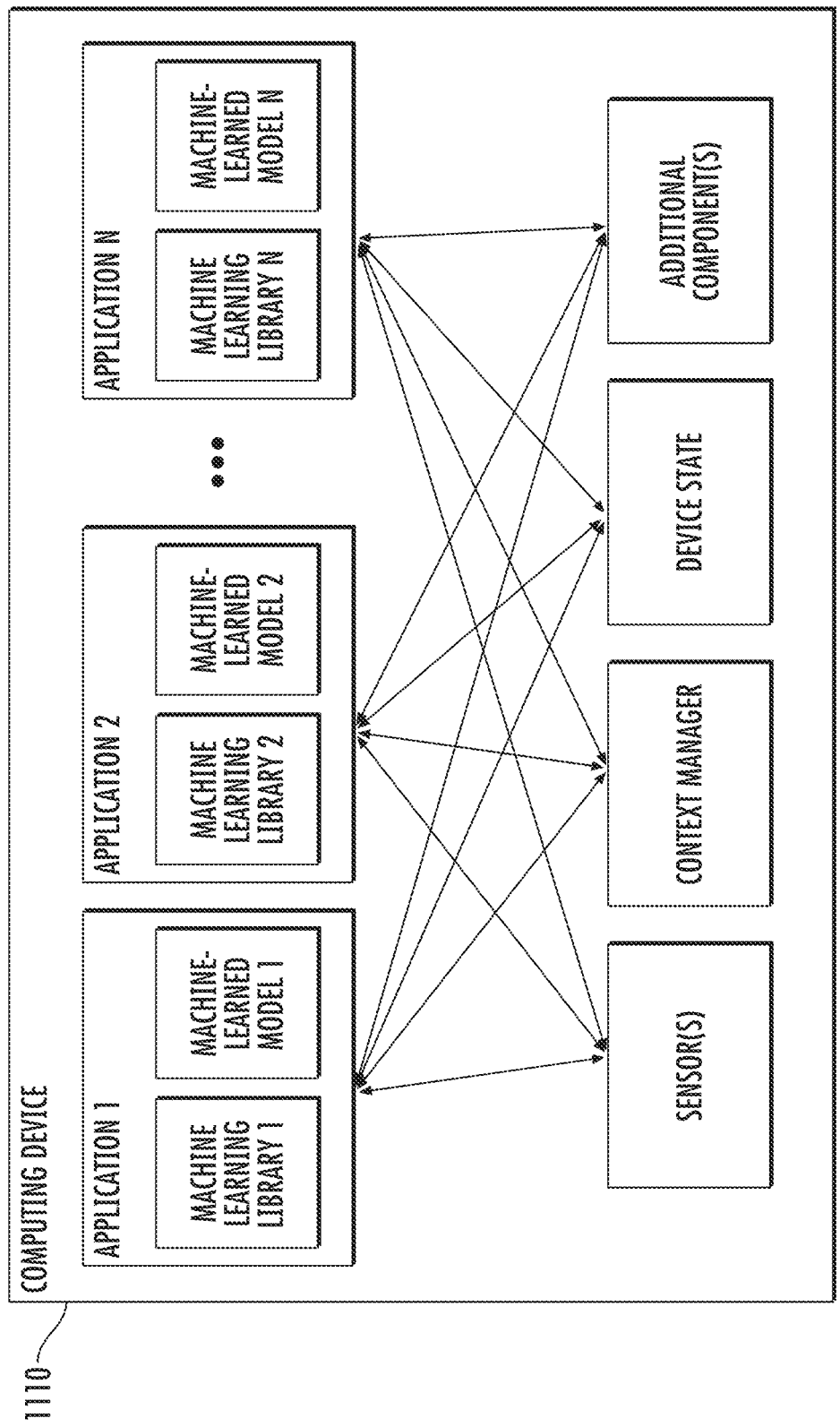
FIG. 18 depicts a block diagram of an example computing device that can be used to implement example embodiments in accordance with the present disclosure.

FIG. 18 illustrates one example computing system that can be used to implement the present disclosure. Other computing systems can be used as well. For example, in some implementations, the user computing device 1002 can include the model trainer 1060 and the training data 1062. In such implementations, the machine learned model 1020 can be both trained and used locally at the user computing device 1002. In some of such implementations, the user computing device 1002 can implement the model trainer 1060 to personalize the machine learned model 1020 based on user-specific data.

Figure 19:
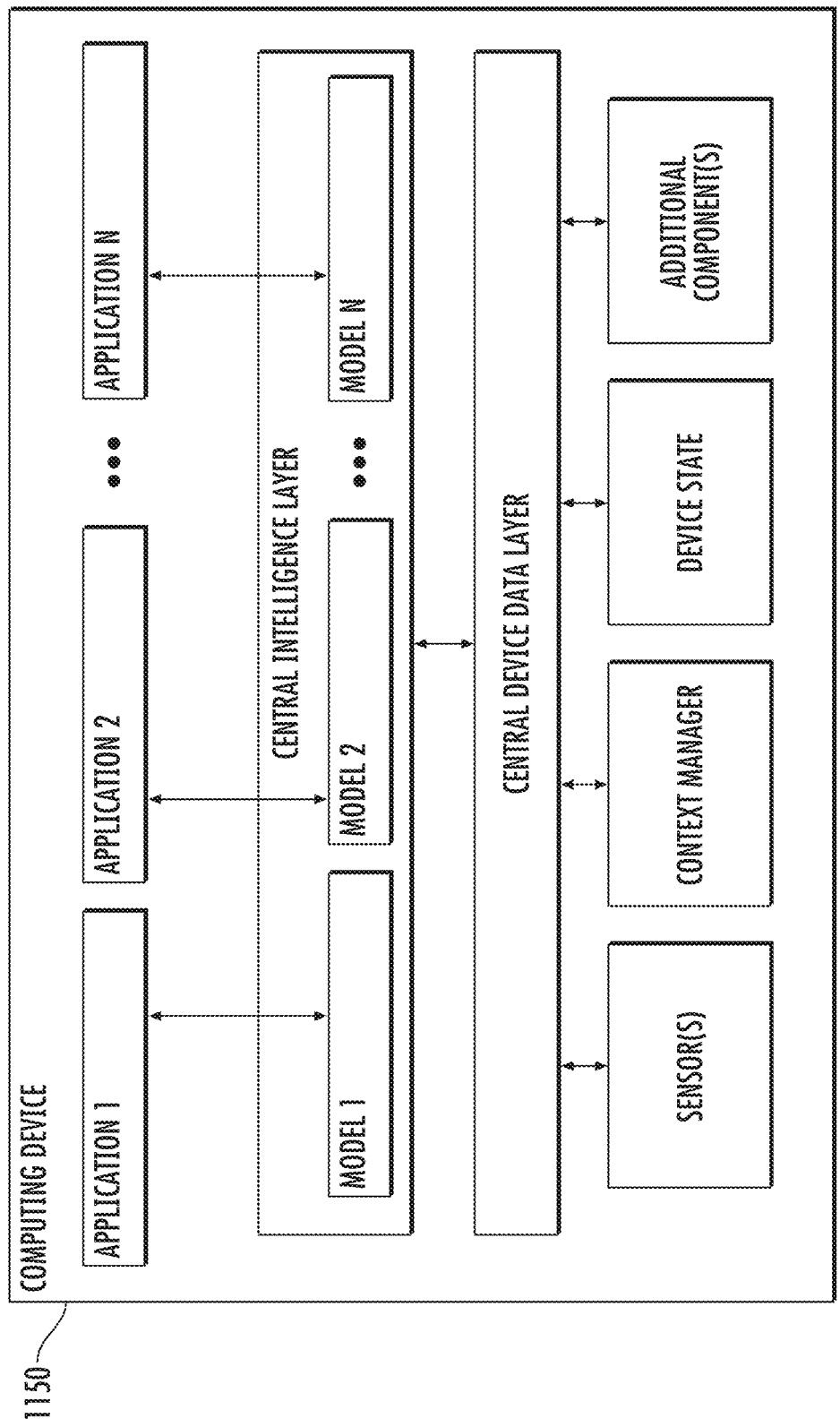
FIG. 19 depicts a block diagram of an example computing device that can be used to implement example embodiments in accordance with the present disclosure.

FIG. 19 depicts a block diagram of an example computing device 1110 that performs according to example embodiments of the present disclosure. The computing device 1110 can be a user computing device or a server computing device.

The computing device 1110 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 19, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

FIG. 19 depicts a block diagram of an example computing device 1150 that performs according to example embodiments of the present disclosure. The computing device 1150 can be a user computing device or a server computing device.

The computing device 1150 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 19, a respective machine-learned model (e.g., a model) can be provided for each application and managed by the central intelligence layer. In other implementations, two or more applications can share a single machine-learned model. For example, in some implementations, the central intelligence layer can provide a single model (e.g., a single model) for all of the applications. In some implementations, the central intelligence layer is included within or otherwise implemented by an operating system of the computing device 1150.

The central intelligence layer can communicate with a central device data layer. The central device data layer can be a centralized repository of data for the computing device 1150. As illustrated in FIG. 19, the central device data layer can communicate with a number of other components of the computing device, such as, for example, one or more sensors, a context manager, a device state component, and/or additional components. In some implementations, the central device data layer can communicate with each device component using an API (e.g., a private API).

The technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A computer-implemented method for generating skin condition diagnostics, comprising:
    authenticating, by one or more processors of a user computing device, a user via a fingerprint scan of a first skin region of the user using a three-dimensional (3D) sonic sensor of the user computing device;
    generating, by the one or more processors, a three-dimensional (3D) volumetric sonic measurement of a second skin region of the user based at least in part on one or more sonic pulses of the 3D sonic sensor;
    inputting, by the one or more processors, data indicative of the 3D volumetric sonic measurement into one or more machine-learning models configured to identify one or more skin conditions in response to one or more 3D volumetric sonic measurement inputs;
    generating, by the one or more processors based on one or more outputs of the one or more machine-learned models, one or more skin condition identifications associated with the second skin region of the user; and
    providing, by the user computing device, one or more outputs including the one or more skin condition identifications associated with the second skin region of the user.

2. The computer-implemented method of claim 1, wherein generating, by the one or more processors, a three-dimensional (3D) volumetric sonic measurement of the second skin region of the user using the 3D sonic sensor, comprises:
    generating two-dimensional sonic measurement data based at least in part on back-reflection associated with one or more sonic pulses contacting an outer surface of the second skin region of the user; and
    generating depth ultrasonic measurement data based at least in part on time-resolving back-reflection associated with sub-surface scattering of one or more sonic pulses entering a below-surface region of the second skin region of the user.

3. The computer-implemented method of claim 2, wherein authenticating, by one or more processors of the user computing device, the user via the fingerprint scan of the first skin region of the user using the 3D sonic sensor of the user computing device comprises:
    generating two-dimensional sonic measurement data based at least in part on back-reflection associated with one or more sonic pulses contacting an outer surface of the second skin region of the user while ignoring time-resolution of back-reflection associated with sub-surface scattering.

4. The computer-implemented method of claim 2, wherein generating depth sonic measurement data based at least in part on time-resolving back-reflection associated with sub-surface scattering of one or more sonic pulses entering the below-surface region of the second skin region of the user comprises:
    converting back-reflected timing information into distance based on scaling by a speed of sound.

5. The computer-implemented method of claim 2, wherein:
    the 3D sonic sensor comprises a two-dimensional array of transducers that transmit and receive sonic signals;
    generating two-dimensional ultrasonic measurement data based at least in part on back-reflection associated with one or more sonic pulses contacting the outer surface of the second skin region of the user comprises beam-forming to increase a resolution of the two-dimensional array.

6. The computer-implemented method of claim 2, wherein:
    the back-reflection associated with sub-surface scattering of one or more ultrasonic pulses entering the below-surface region of the second skin region of the user includes an integral energy of pulses that are backreflected by at least one of an epidermal layer or a dermal layer below a surface of the second skin region of the user.

7. The computer-implemented method of claim 1, wherein:
the one or more machine-learned models include a dictionary of skin condition features in a 3D sonic volumetric domain; and
the method further comprises generating, by the one or more processors, the one or more outputs of the one or more machine-learned models by enforcing an optimization to identify at least one feature in the dictionary that minimizes an error between the data indicative of the 3D volumetric sonic measurement and the dictionary of skin condition features.

8. The computer-implemented method of claim 7, wherein:
the 3D sonic sensor of the user computing device comprises a first number of transducers; and
the dictionary of skin condition features includes data based on a second three-dimensional sonic sensor having a greater, second number of transducers.

9. The computer-implemented method of claim 8, wherein identifying at least one feature in the dictionary that minimizes the error between the data indicative of the 3D volumetric sonic measurement and the dictionary of skin condition features comprises:
applying a voxel blurring simulation to the dictionary of skin condition features to simulate voxel blurring associated with the 3D sonic sensor of the user computing device.

10. The computer-implemented method of claim 7, wherein generating, by the one or more processors based on an output of the one or more machine-learned models, one or more inferences of skin condition associated with the second skin region of the user comprises:
generating a confidence value based at least in part on the error between the data indicative of the 3D volumetric sonic measurement and the dictionary of skin condition features.

11. The computer-implemented method of claim 1, wherein:
the one or more machine-learned models include a classification model trained to identify one or more skin conditions based on a classification of 3D sonic volumetric data;
the method further comprises generating, by the one or more processors, the one or more outputs of the one or more machine-learned models by classifying the data indicative of the 3D volumetric sonic measurement and generating one or more inferences associated with the one or more skin conditions.

12. The computer-implemented method of claim 1, further comprising training, by one or more second processors, the one or more machine-learning models using training data that includes 3-D sonic volumetric data labeled to indicate a presence or non-presence of skin cancer.

13. The computer-implemented method of claim 12, wherein training, by one or more second processors, the one or more machine-learning models using training data that includes 3-D sonic volumetric data labeled to indicate a presence or non-presence of skin cancer comprises:
obtaining data descriptive of the one or more machine-learning models;
providing a first portion of one or more sets of training data as input to the one or more machine-learning models, the first portion of the one or more sets of training data including sensor data associated with one or more sensors;
obtaining, as output of the one or more machine-learning models, data indicative of a skin cancer condition based on the first portion of the one or more sets of training data;
determining one or more loss functions based at least in part of output of the one or more machine-learning models and a second portion of the one or more sets of training data; and
modifying at least a portion of the one or more machine-learning models based at least in part on the one or more loss functions.

14. The computer-implemented method of claim 13, wherein:
the first portion of the one or more sets of training data include sensor data associated with a melanoma; and
the second portion of the one or more sets of training data include an annotation indicative of the melanoma.

15. The computer-implemented method of claim 1, wherein:
the user computing device is a smartphone.

16. The computer-implemented method of claim 1, wherein:
the 3D sonic sensor is a 3D ultrasonic sensor; and
the 3D volumetric sonic measurement is a 3D volumetric ultrasonic measurement.

17. A computing device, comprising:
one or more three-dimensional (3D) sonic sensors;
one or more processors;
one or more non-transitory computer-readable media that collectively store instructions that when executed by the one or more processors cause the one or more processors to perform operations, the operations comprising:
generating a three-dimensional (3D) volumetric sonic measurement of a skin region of a user based at least in part on one or more sonic pulses of the one or more 3D sonic sensors;
inputting data indicative of the 3D volumetric sonic measurement into one or more machine-learning models configured to identify one or more skin conditions in response to one or more 3D volumetric sonic measurement inputs;
generating, based on one or more outputs of the one or more machine-learned models, one or more skin condition identifications associated with the skin region of the user; and
providing one or more outputs including the one or more skin condition identifications associated with the skin region of the user.

18. The computing device of claim 17, wherein generating a three-dimensional (3D) volumetric sonic measurement of the skin region of the user using the 3D sonic sensor, comprises:
generating two-dimensional sonic measurement data based at least in part on back-reflection associated with one or more sonic pulses contacting an outer surface of the skin region of the user; and
generating depth ultrasonic measurement data based at least in part on time-resolving back-reflection associated with sub-surface scattering of one or more sonic pulses entering a below-surface region of the skin region of the user.

19. One or more non-transitory computer-readable media storing computer instructions, that when executed by one or more processors, cause the one or more processors to perform operations, the operations comprising:
- generating a three-dimensional (3D) volumetric sonic measurement of a skin region of a user based at least in part on one or more sonic pulses of one or more 3D sonic sensors;
- inputting data indicative of the 3D volumetric sonic measurement into one or more machine-learning models configured to identify one or more skin conditions in response to one or more 3D volumetric sonic measurement inputs;
- generating, based on one or more outputs of the one or more machine-learned models, one or more skin condition identifications associated with the skin region of the user; and
- providing one or more outputs including the one or more skin condition identifications associated with the skin region of the user.

20. The one or more non-transitory computer-readable media of claim 19, wherein generating a three-dimensional (3D) volumetric sonic measurement of the skin region of the user using the one or more 3D sonic sensors, comprises:
- generating two-dimensional sonic measurement data based at least in part on back-reflection associated with one or more sonic pulses contacting an outer surface of the skin region of the user; and
- generating depth ultrasonic measurement data based at least in part on time-resolving back-reflection associated with sub-surface scattering of one or more sonic pulses entering a below-surface region of the skin region of the user.

\* \* \* \* \*